US012806203B2

(12) United States Patent
Parikh et al.

(10) Patent No.: US 12,806,203 B2
(45) **Date of Patent: *Nov. 24, 2026**

(54) TOPICAL FORMULATION FOR A JAK INHIBITOR

(71) Applicant: Incyte Corporation, Wilmington, DE (US)

(72) Inventors: Bhavnish Parikh, Avondale, PA (US); Bhavesh Shah, San Antonio, TX (US); Krishnaswamy Yeleswaram, Landenberg, PA (US)

(73) Assignees: Incyte Corporation, Wilmington, DE (US); Incyte Holdings Corporation, Wilmington, DE (US)

( * ) Notice: Subject to any disclaimer, the term of this patent is extended or adjusted under 35 U.S.C. 154(b) by 24 days.

This patent is subject to a terminal disclaimer.

(21) Appl. No.: 18/089,651

(22) Filed: Dec. 28, 2022

(65) Prior Publication Data

US 2023/0277541 A1 Sep. 7, 2023

Related U.S. Application Data

(60) Continuation of application No. 17/541,439, filed on Dec. 3, 2021, now Pat. No. 12,622,908, which is a continuation of application No. 16/948,408, filed on Sep. 17, 2020, now Pat. No. 11,219,624, which is a continuation of application No. 16/947,735, filed on Aug. 14, 2020, now Pat. No. 10,869,870, which is a division of application No. 16/566,625, filed on Sep. 10, 2019, now Pat. No. 10,758,543, which is a continuation of application No. 14/714,820, filed on May 18, 2015, now abandoned, which is a continuation of application No. 13/112,370, filed on May 20, 2011, now abandoned.

(60) Provisional application No. 61/347,132, filed on May 21, 2010.

(51) Int. Cl.

| | |
|---|---|
| ***A61K 31/519*** | (2006.01) |
| ***A61K 9/00*** | (2006.01) |
| ***A61K 9/06*** | (2006.01) |
| ***A61K 9/107*** | (2006.01) |
| ***A61K 47/06*** | (2006.01) |
| ***A61K 47/10*** | (2017.01) |
| ***A61K 47/14*** | (2017.01) |
| ***A61K 47/24*** | (2006.01) |
| ***A61K 47/26*** | (2006.01) |
| ***A61K 47/36*** | (2006.01) |
| ***A61P 17/00*** | (2006.01) |
| ***A61P 17/06*** | (2006.01) |

(52) U.S. Cl.

CPC .......... *A61K 31/519* (2013.01); *A61K 9/0014* (2013.01); *A61K 9/06* (2013.01); *A61K 9/107* (2013.01); *A61K 47/06* (2013.01); *A61K 47/10* (2013.01); *A61K 47/14* (2013.01); *A61K 47/24* (2013.01); *A61K 47/26* (2013.01); *A61K 47/36* (2013.01); *A61P 17/00* (2018.01); *A61P 17/06* (2018.01)

(58) Field of Classification Search

CPC ...... A61K 31/619; A61K 9/107; A61K 47/06; A61K 47/10; A61K 47/14; A61K 47/24; A61K 47/26; A61K 47/36

See application file for complete search history.

(56) References Cited

U.S. PATENT DOCUMENTS

2008/0207570 A1* 8/2008 Segura-Orsoni ....... A61K 47/14 514/180
2008/0312259 A1* 12/2008 Rodgers .................. A61P 35/02 544/280

OTHER PUBLICATIONS

English Translation of Main Text of Request for Patent Invalidation for Chinese Patent No. ZL201180035301.2, dated Jul. 25, 2025 (69 pages).
English Translation of Main Text of Request for Patent Invalidation for Chinese Patent No. ZL201610207261.X, dated Jul. 25, 2025 (73 pages).
English Translation of Supplementary Opinion by the Petitioner in Invalidation Proceedings for Chinese Patent No. ZL201180035301.2 (Case No. 4W120582), dated Aug. 22, 2025 (7 pages).

* cited by examiner

*Primary Examiner* — Layla Soroush
(74) *Attorney, Agent, or Firm* — Finnegan, Henderson, Farabow, Garrett & Dunner, LLP

(57) ABSTRACT

This invention relates to pharmaceutical formulations for topical skin application comprising (R)-3-cyclopentyl-3-[4-(7H-pyrrolo[2,3-d]pyrimidin-4-yl)-1H-pyrazol-1-yl]propanenitrile, or a pharmaceutically acceptable salt thereof, and use in the treatment of skin disorders.

10 Claims, 7 Drawing Sheets

(a) (b)

(b)

(a)

(a) (b)

(a)

(b)

(a) (b)

TOPICAL FORMULATION FOR A JAK INHIBITOR

This is a continuation of U.S. Ser. No. 17/541,439, filed Dec. 3, 2021, which is continuation of U.S. Ser. No. 16/948,408, filed Sep. 17, 2020, now U.S. U.S. Pat. No. 11,219,624, which is a continuation of U.S. Ser. No. 16/947,735, filed Aug. 14, 2020, now U.S. Pat. No. 10,869,870, which is a divisional of U.S. Ser. No. 16/566,625, filed Sep. 10, 2019, now U.S. Pat. No. 10,758,543, which is a continuation application of U.S. Ser. No. 14/714,820, filed May 18, 2015, now abandoned, which is a continuation of U.S. Ser. No. 13/112,370, filed May 20, 2011, now abandoned, which claims the benefit and priority of U.S. Provisional Application 61/347,132, filed May 21, 2010, each of which is incorporated herein by reference in its entirety.

TECHNICAL FIELD

This invention relates to pharmaceutical formulations for topical skin application comprising (R)-3-cyclopentyl-3-[4-(7H-pyrrolo[2,3-d]pyrimidin-4-yl)-1H-pyrazol-1-yl]propanenitrile, or a pharmaceutically acceptable salt thereof, and use in the treatment of skin disorders.

BACKGROUND

Protein kinases (PKs) regulate diverse biological processes including cell growth, survival, differentiation, organ formation, morphogenesis, neovascularization, tissue repair, and regeneration, among others. Protein kinases also play specialized roles in a host of human diseases including cancer. Cytokines, low-molecular weight polypeptides or glycoproteins, regulate many pathways involved in the host inflammatory response to sepsis. Cytokines influence cell differentiation, proliferation and activation, and can modulate both pro-inflammatory and anti-inflammatory responses to allow the host to react appropriately to pathogens. Signaling of a wide range of cytokines involves the Janus kinase family (JAKs) of protein tyrosine kinases and Signal Transducers and Activators of Transcription (STATs). There are four known mammalian JAKs: JAK1 (Janus kinase-1), JAK2, JAK3 (also known as Janus kinase, leukocyte; JAKL; and L-JAK), and TYK2 (protein-tyrosine kinase 2).

Cytokine-stimulated immune and inflammatory responses contribute to pathogenesis of diseases: pathologies such as severe combined immunodeficiency (SCID) arise from suppression of the immune system, while a hyperactive or inappropriate immune/inflammatory response contributes to the pathology of autoimmune diseases (e.g., asthma, systemic lupus erythematosus, thyroiditis, myocarditis), and illnesses such as scleroderma and osteoarthritis (Ortmann, R. A., T. Cheng, et al. (2000) *Arthritis Res* 2(1): 16-32).

Deficiencies in expression of JAKs are associated with many disease states. For example, Jak1−/− mice are runted at birth, fail to nurse, and die perinatally (Rodig, S. J., M. A. Meraz, et al. (1998) *Cell* 93(3): 373-83). Jak2−/− mouse embryos are anemic and die around day 12.5 postcoitum due to the absence of definitive erythropoiesis.

The JAK/STAT pathway, and in particular all four JAKs, are believed to play a role in the pathogenesis of asthmatic response, chronic obstructive pulmonary disease, bronchitis, and other related inflammatory diseases of the lower respiratory tract. Multiple cytokines that signal through JAKs have been linked to inflammatory diseases/conditions of the upper respiratory tract, such as those affecting the nose and sinuses (e.g., rhinitis and sinusitis) whether classically allergic reactions or not. The JAK/STAT pathway has also been implicated in inflammatory diseases/conditions of the eye and chronic allergic responses.

Activation of JAK/STAT in cancers may occur by cytokine stimulation (e.g. IL-6 or GM-CSF) or by a reduction in the endogenous suppressors of JAK signaling such as SOCS (suppressor or cytokine signaling) or PIAS (protein inhibitor of activated STAT) (Boudny, V., and Kovarik, J., *Neoplasm.* 49:349-355, 2002). Activation of STAT signaling, as well as other pathways downstream of JAKs (e.g., Akt), has been correlated with poor prognosis in many cancer types (Bowman, T., et al. *Oncogene* 19:2474-2488, 2000). Elevated levels of circulating cytokines that signal through JAK/STAT play a causal role in cachexia and/or chronic fatigue. As such, JAK inhibition may be beneficial to cancer patients for reasons that extend beyond potential anti-tumor activity.

Inhibition of the JAK kinases is also envisioned to have therapeutic benefits in patients suffering from skin immune disorders such as psoriasis, and skin sensitization. In psoriasis vulgaris, the most common form of psoriasis, it has been generally accepted that activated T lymphocytes are important for the maintenance of the disease and its associated psoriatic plaques (Gottlieb, A. B., et al, *Nat Rev Drug Disc.,* 4:19-34). Psoriatic plaques contain a significant immune infiltrate, including leukocytes and monocytes, as well as multiple epidermal layers with increased keratinocyte proliferation. While the initial activation of immune cells in psoriasis occurs by an ill defined mechanism, the maintenance is believed to be dependent on a number of inflammatory cytokines, in addition to various chemokines and growth factors (JCI, 113:1664-1675). Many of these, including interleukins-2, -4, -6, -7, -12, -15, -18, and -23 as well as GM-CSF and IFNg, signal through the Janus (JAK) kinases (*Adv Pharmacol.* 2000; 47:113-74). As such, blocking signal transduction at the level of JAK kinases may result in therapeutic benefits in patients suffering from psoriasis or other immune disorders of the skin.

Given the usefulness of JAK inhibitors in the treatment of skin disorders, there is a need for improved topical formulations of JAK inhibitors. In particular, there is a need for stable, easily applied formulations for JAK inhibitors with good skin permeation characteristics. The formulations of the invention, as well the methods described herein are directed toward this need and other ends.

SUMMARY

A potent JAK1/JAK2 inhibitor, (R)-3-(4-(7H-pyrrolo[2,3-d]pyrimidin-4-yl)-1H-pyrazol-1-yl)-3-cyclopentylpropanenitrile, and its pharmaceutically acceptable salts, has previously been described in U.S. Pat. No. 7,598,257, U.S. Patent Publ. No. 2009/0181959, and U.S. Patent Publ. No. 2008/0312259, each of which is incorporated herein by reference in its entirety. The present invention describes an oil-in-water formulation of (R)-3-(4-(7H-pyrrolo[2,3-d]pyrimidin-4-yl)-1H-pyrazol-1-yl)-3-cyclopentylpropanenitrile suitable for topical administration and treatment of skin disorders.

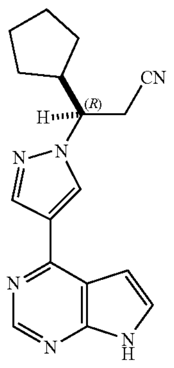

Accordingly, the present invention provides, inter alia, a pharmaceutical formulation for topical skin application, comprising:

an oil-in-water emulsion; and a therapeutically effective amount of a therapeutic agent which is (R)-3-cyclopentyl-3-[4-(7H-pyrrolo[2,3-d]pyrimidin-4-yl)-1H-pyrazol-1-yl]propanenitrile, or a pharmaceutically acceptable salt thereof.

The present invention also provides a method of treating a skin disorder, comprising applying a pharmaceutical formulation described herein to an area of skin of the patient.

The present invention also provides a pharmaceutical formulation described herein for use in treatment of a skin disorder in a patient in need thereof.

The present invention also provides use of a pharmaceutical formulation described herein for the preparation of a medicament for use in treatment of a skin disorder in a patient in need thereof.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
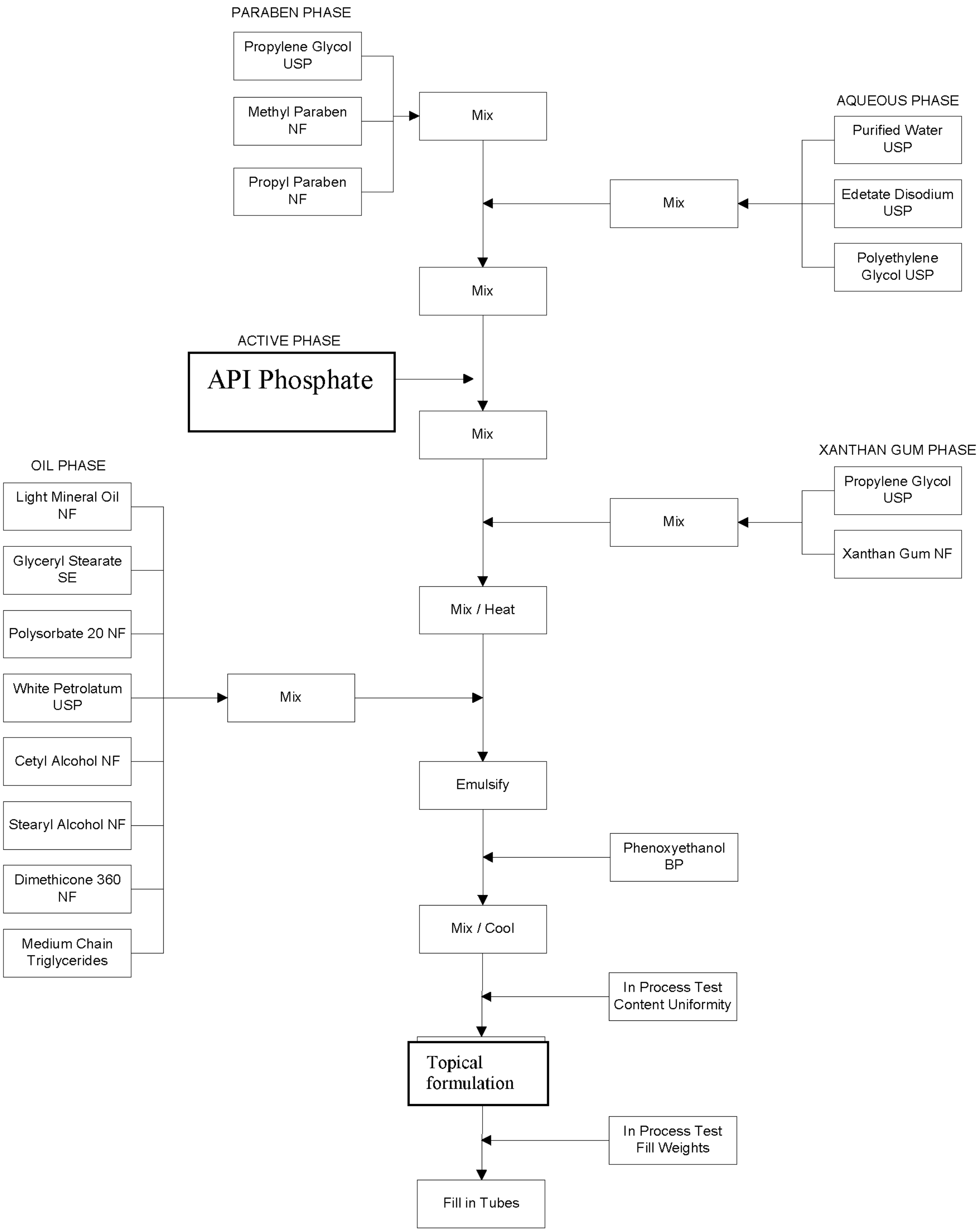
FIG. 1 depicts a flowchart describing the manufacturing process for an oil-in-water formulation of (R)-3-(4-(7H-pyrrolo[2,3-d]pyrimidin-4-yl)-1H-pyrazol-1-yl)-3-cyclopentylpropanenitrile phosphoric acid salt.

Accordingly, the present invention provides, inter alia, a pharmaceutical formulation for topical skin application, comprising a therapeutically effective amount of (R)-3-cyclopentyl-3-[4-(7H-pyrrolo[2,3-d]pyrimidin-4-yl)-1H-pyrazol-1-yl]propanenitrile, or a pharmaceutically acceptable salt thereof.

In some embodiments, the pharmaceutical formulation comprises:

an oil-in-water emulsion; and a therapeutically effective amount of a therapeutic agent which is (R)-3-cyclopentyl-3-[4-(7H-pyrrolo[2,3-d]pyrimidin-4-yl)-1H-pyrazol-1-yl]propanenitrile, or a pharmaceutically acceptable salt thereof.

In some embodiments, the emulsion comprises water, an oil component, and an emulsifier component.

As used herein, the term "emulsifier component" refers, in one aspect, to a substance, or mixtures of substances that maintains an element or particle in suspension within a fluid medium. In some embodiments, the emulsifier component allows an oil phase to form an emulsion when combined with water. In some embodiments, the emulsifier component refers to one or more non-ionic surfactants.

The oil-in-water formulations were found to have better appearance, spreadability and stability as compared with other formulations. The formulations have a thick, creamy appearance which allows for good spreadability of the formulation on skin. This good spreadability leads to better skin permeation than comparable anhydrous formulations. For example, the oil-in-water formulations showed higher cumulative amounts in studies of transport across human cadaver skin over 24 hours when compared with an anhydrous ointment. While not wishing to be bound by any particular theory, the higher cumulative amounts are believed to be due to better spreadability of the oil-in-water formulation as compared to the anhydrous ointment, resulting in increased surface area for transport. A higher viscosity for the oil-in-water formulations also appeared to be preferred with respect to skin permeation as higher viscosity cream formulations had better transport across human cadaver skin as compared with oil-in-water lotions of lower viscosity.

The oil-in-water formulations described herein were found to have good stability over a three-month period when stored at 25° C./60% RH and 40° C./75% RH in aluminum tubes and maintain reasonable viscosity over time. By comparison, the water-in-oil formulations displayed syneresis when stored at 40° C. (syneresis means separation of liquid from the emulsion).

The water-in-oil formulation was also less desirable than the formulations of the invention, because the API dissolved in the base over time, leading to highly variable skin permeation in in vitro studies as well as a lack of an increase in permeability with increasing strength of the formulation.

In transport studies with freshly excised mouse skin, the oil-in-water formulations also displayed a general trend of increased permeability when the strength of the solubilized cream was increased from 0.5% w/w to 1.5% w/w, while such a trend was not seen with the water-in-oil formulations. Thus, it appears that the water-in-oil emulsions will not have any advantage in terms of providing enhanced permeation with increasing strengths.

Further, the formulations described herein are relatively simple to manufacture with a repeatable process of formulation. The resultant product is easily packaged. The formulations appear to have good stability and relatively consistent permeation profiles.

In some embodiments, the oil component is present in an amount of about 10% to about 40% by weight of the formulation.

In some embodiments, the oil component is present in an amount of about 17% to about 27% by weight of the formulation.

In some embodiments, the oil component is present in an amount of about 20% to about 27% by weight of the formulation.

In some embodiments, the oil component comprises one or more substances independently selected from petrolatums, fatty alcohols, mineral oils, triglycerides, and silicone oils.

In some embodiments, the oil component comprises one or more substances independently selected from white petrolatum, cetyl alcohol, stearyl alcohol, light mineral oil, medium chain triglycerides, and dimethicone.

In some embodiments, the oil component comprises an occlusive agent component.

In some embodiments, the occlusive agent component is present in an amount of about 2% to about 15% by weight of the formulation.

In some embodiments, the occlusive agent component is present in an amount of about 5% to about 10% by weight of the formulation.

As used herein, the term "occlusive agent component" refers to a hydrophobic agent or mixtures of hydrophobic agents that form an occlusive film on skin that reduces transepidermal water loss (TEWL) by preventing evaporation of water from the stratum corneum.

In some embodiments, the occlusive agent component comprises one or more substances selected from fatty acids (e.g., lanolin acid), fatty alcohols (e.g., lanolin alcohol), hydrocarbon oils & waxes (e.g., petrolatum), polyhydric alcohols (e.g., propylene glycol), silicones (e.g., dimethicone), sterols (e.g., cholesterol). vegetable or animal fat (e.g., cocoa butter), vegetable wax (e.g., Carnauba wax), and wax ester (e.g., bees wax).

In some embodiments, the occlusive agent component comprises one or more substances selected from lanolin acid fatty alcohols, lanolin alcohol, petrolatum, propylene glycol, dimethicone, cholesterol, cocoa butter, Carnauba wax, and bees wax.

In some embodiments, the occlusive agent component comprises petrolatum.

In some embodiments, the occlusive agent component comprises white petrolatum.

In some embodiments, the oil component comprises a stiffening agent component.

In some embodiments, the stiffening agent component is present in an amount of about 2% to about 8% by weight of the formulation.

In some embodiments, the stiffening agent component is present in an amount of about 3% to about 6% by weight of the formulation.

In some embodiments, the stiffening agent component is present in an amount of about 4% to about 7% by weight of the formulation.

As used herein, the term "stiffening agent component" refers to a substance or mixture of substances that increases the viscosity and/or consistency of the formulation or improves the rheology of the formulation.

In some embodiments, the stiffening agent component comprises one or more substances independently selected from fatty alcohols.

In some embodiments, the stiffening agent component comprises one or more substances independently selected from $C_{12-20}$ fatty alcohols.

In some embodiments, the stiffening agent component comprises one or more substances independently selected from $C_{16-18}$ fatty alcohols.

In some embodiments, the stiffening agent component comprises one or more substances independently selected from cetyl alcohol and stearyl alcohol.

In some embodiments, the oil component comprises an emollient component.

In some embodiments, the emollient component is present in an amount of about 5% to about 15% by weight of the formulation.

In some embodiments, the emollient component is present in an amount of about 7% to about 13% by weight of the formulation.

As used herein, the term "emollient component" refers to an agent that softens or soothes the skin or soothes an irritated internal surface.

In some embodiments, the emollient component comprises one or more substances independently selected from mineral oils and triglycerides.

In some embodiments, the emollient component comprises one or more substances independently selected from light mineral oil and medium chain triglycerides.

In some embodiments, the emollient component comprises one or more substances independently selected from light mineral oil, medium chain triglycerides, and dimethicone.

In some embodiments, the water is present in an amount of about 35% to about 65% by weight of the formulation.

In some embodiments, the water is present in an amount of about 40% to about 60% by weight of the formulation.

In some embodiments, the water is present in an amount of about 45% to about 55% by weight of the formulation.

In some embodiments, the emulsifier component is present in an amount of about 1% to about 9% by weight of the formulation.

In some embodiments, the emulsifier component is present in an amount of about 2% to about 6% by weight of the formulation.

In some embodiments, the emulsifier component is present in an amount of about 3% to about 5% by weight of the formulation.

In some embodiments, the emulsifier component is present in an amount of about 4% to about 7% by weight of the formulation.

In some embodiments, the pharmaceutical formulation comprises an emulsifier component and a stiffening agent component, wherein the combined amount of emulsifier component and stiffening agent component is at least about 8% by weight of the formulation.

In some embodiments, the emulsifier component comprises one or more substances independently selected from glyceryl fatty esters and sorbitan fatty esters.

In some embodiments, the emulsifier component comprises one or more substances independently selected from glyceryl stearate, and polysorbate 20.

In some embodiments, the pharmaceutical formulation further comprises a stabilizing agent component.

In some embodiments, the stabilizing agent component is present in an amount of about 0.05% to about 5% by weight of the formulation.

In some embodiments, the stabilizing agent component is present in an amount of about 0.1% to about 2% by weight of the formulation.

In some embodiments, the stabilizing agent component is present in an amount of about 0.3 to about 0.5% by weight of the formulation.

As used herein, the term "stabilizing agent component" refers to a substance or mixture of substances that improves the stability of the pharmaceutical formulation and/or the compatibility of the components in the formulation. In some embodiments, the stabilizing agent component prevents agglomeration of the emulsion and stabilizes the droplets in the oil-in-water emulsion.

In some embodiments, the stabilizing agent component comprises one or more substances independently selected from polysaccharides.

In some embodiments, the stabilizing agent component comprises xanthan gum.

In some embodiments, the pharmaceutical formulation further comprises a solvent component.

In some embodiments, the solvent component is present in an amount of about 10% to about 35% by weight of the formulation.

In some embodiments, the solvent component is present in an amount of about 15% to about 30% by weight of the formulation.

In some embodiments, the solvent component is present in an amount of about 20% to about 25% by weight of the formulation.

As used herein, the term "solvent component" is a liquid substance or mixture of liquid substances capable of dissolving (R)-3-(4-(7H-pyrrolo[2,3-d]pyrimidin-4-yl)-1H-pyrazol-1-yl)-3-cyclopentylpropanenitrile or other substances in the formulation. In some embodiments, the solvent component is a liquid substance or mixture of liquid substances in which (R)-3-(4-(7H-pyrrolo[2,3-d]pyrimidin-4-yl)-1H-pyrazol-1-yl)-3-cyclopentylpropanenitrile, or its pharmaceutically acceptable salt, has reasonable solubility. For example, solubilities of (R)-3-(4-(7H-pyrrolo[2,3-d]pyrimidin-4-yl)-1H-pyrazol-1-yl)-3-cyclopentylpropanenitrile (free base) or its phosphate salt are reported in Table 21. In some embodiments, a solvent is a substance or mixture thereof, in which (R)-3-(4-(7H-pyrrolo[2,3-d]pyrimidin-4-yl)-1H-pyrazol-1-yl)-3-cyclopentylpropanenitrile, or its pharmaceutically acceptable salt (whichever is used), has a solubility of at least about 10 mg/mL or greater, at least about 15 mg/mL or greater, or at least about 20 mg/mL or greater, when measured as described in Example 4.

In some embodiments, the solvent component comprises one or more substances independently selected from alkylene glycols and polyalkylene glycols.

In some embodiments, the solvent component comprises one or more substances independently selected from propylene glycol and polyethylene glycol.

In some embodiments, the therapeutic agent is present in an amount of about 0.5% to about 1.5% by weight of the formulation on a free base basis.

In some embodiments, the therapeutic agent is present in an amount of about 0.5% by weight of the formulation on a free base basis.

In some embodiments, the therapeutic agent is present in an amount of about 1% by weight of the formulation on a free base basis.

In some embodiments, the therapeutic agent is present in an amount of about 1.5% by weight of the formulation on a free base basis.

In some embodiments, the therapeutic agent is (R)-3-cyclopentyl-3-[4-(7H-pyrrolo[2,3-d]pyrimidin-4-yl)-1H-pyrazol-1-yl]propanenitrile phosphate.

In some embodiments, the pharmaceutical formulation comprises:

- from about 35% to about 65% of water by weight of the formulation;
- from about 10% to about 40% of an oil component by weight of the formulation;
- from about 1% to about 9% of an emulsifier component by weight of the formulation;
- from about 10% to about 35% of a solvent component by weight of the formulation;
- from about 0.05% to about 5% of a stabilizing agent component by weight of the formulation; and
- from about 0.5% to about 1.5% of (R)-3-cyclopentyl-3-[4-(7H-pyrrolo[2,3-d]pyrimidin-4-yl)-1H-pyrazol-1-yl]propanenitrile, or a pharmaceutically acceptable salt thereof, by weight of the formulation on a free base basis.

In some embodiments, the pharmaceutical formulation comprises:

- from about 40% to about 60% of water by weight of the formulation;
- from about 15% to about 30% of an oil component by weight of the formulation;
- from about 2% to about 6% of an emulsifier component by weight of the formulation;
- from about 15% to about 30% of a solvent component by weight of the formulation;
- from about 0.1% to about 2% of a stabilizing agent component by weight of the formulation; and
- from about 0.5% to about 1.5% of (R)-3-cyclopentyl-3-[4-(7H-pyrrolo[2,3-d]pyrimidin-4-yl)-1H-pyrazol-1-yl]propanenitrile, or a pharmaceutically acceptable salt thereof, by weight of the formulation on a free base basis.

In some embodiments, the pharmaceutical formulation comprises:

- from about 45% to about 55% of water by weight of the formulation;
- from about 17% to about 27% of an oil component by weight of the formulation;
- from about 3% to about 5% of an emulsifier component by weight of the formulation;
- from about 20% to about 25% of a solvent component by weight of the formulation;
- from about 0.3% to about 0.5% of a stabilizing agent component by weight of the formulation; and
- from about 0.5% to about 1.5% of (R)-3-cyclopentyl-3-[4-(7H-pyrrolo[2,3-d]pyrimidin-4-yl)-1H-pyrazol-1-yl]propanenitrile, or a pharmaceutically acceptable salt thereof, by weight of the formulation on a free base basis.

In some embodiments, the pharmaceutical formulation comprises:

from about 45% to about 55% of water by weight of the formulation;

from about 17% to about 27% of an oil component by weight of the formulation;

from about 4% to about 7% of an emulsifier component by weight of the formulation;

from about 20% to about 25% of a solvent component by weight of the formulation;

from about 0.3% to about 0.5% of a stabilizing agent component by weight of the formulation; and from about 0.5% to about 1.5% of (R)-3-cyclopentyl-3-[4-(7H-pyrrolo[2,3-d]pyrimidin-4-yl)-1H-pyrazol-1-yl]propanenitrile, or a pharmaceutically acceptable salt thereof, by weight of the formulation on a free base basis.

In some embodiments:

the oil component comprises one or more substances independently selected from petrolatums, fatty alcohols, mineral oils, triglycerides, and dimethicones;

the emulsifier component comprises one or more substances independently selected from glyceryl fatty esters and sorbitan fatty esters;

the solvent component comprises one or more substances independently selected from alkylene glycols and polyalkylene glycols; and the stabilizing agent component comprises one or more substances independently selected from polysaccharides.

In some embodiments:

the oil component comprises one or more substances independently selected from white petrolatum, cetyl alcohol, stearyl alcohol, light mineral oil, medium chain triglycerides, and dimethicone;

the emulsifier component comprises one or more substances independently selected from glyceryl stearate and polysorbate 20;

the solvent component comprises one or more substances independently selected from propylene glycol and polyethylene glycol; and the stabilizing agent component comprises xanthan gum.

In some embodiments, the pharmaceutical formulation comprises:

from about 35% to about 65% of water by weight of the formulation;

from about 2% to about 15% of an occlusive agent component by weight of the formulation;

from about 2% to about 8% of a stiffening agent component by weight of the formulation;

from about 5% to about 15% of an emollient component by weight of the formulation;

from about 1% to about 9% of an emulsifier component by weight of the formulation;

from about 0.05% to about 5% of a stabilizing agent component by weight of the formulation;

from about 10% to about 35% of a solvent component by weight of the formulation; and from about 0.5% to about 1.5% of (R)-3-cyclopentyl-3-[4-(7H-pyrrolo[2,3-d]pyrimidin-4-yl)-1H-pyrazol-1-yl]propanenitrile, or a pharmaceutically acceptable salt thereof, by weight of the formulation on a free base basis.

In some embodiments, the pharmaceutical formulation comprises:

from about 40% to about 60% of water by weight of the formulation;

from about 5% to about 10% of an occlusive agent component by weight of the formulation;

from about 2% to about 8% of a stiffening agent component by weight of the formulation;

from about 7% to about 12% of an emollient component by weight of the formulation;

from about 2% to about 6% of an emulsifier component by weight of the formulation;

from about 0.1% to about 2% of a stabilizing agent by weight of the formulation;

from about 15% to about 30% of a solvent component by weight of the formulation; and from about 0.5% to about 1.5% of (R)-3-cyclopentyl-3-[4-(7H-pyrrolo[2,3-d]pyrimidin-4-yl)-1H-pyrazol-1-yl]propanenitrile, or a pharmaceutically acceptable salt thereof, by weight of the formulation on a free base basis.

In some embodiments, the pharmaceutical formulation comprises:

from about 45% to about 55% of water by weight of the formulation;

from about 5% to about 10% of an occlusive agent component by weight of the formulation;

from about 3% to about 6% of a stiffening agent component by weight of the formulation;

from about 7% to about 13% of an emollient component by weight of the formulation;

from about 3% to about 5% of an emulsifier component by weight of the formulation;

from about 0.3% to about 0.5% of a stabilizing agent component by weight of the formulation;

from about 20% to about 25% of a solvent component by weight of the formulation; and from about 0.5% to about 1.5% of (R)-3-cyclopentyl-3-[4-(7H-pyrrolo[2,3-d]pyrimidin-4-yl)-1H-pyrazol-1-yl]propanenitrile, or a pharmaceutically acceptable salt thereof, by weight of the formulation on a free base basis.

In some embodiments, the pharmaceutical formulation comprises:

from about 45% to about 55% of water by weight of the formulation;

from about 5% to about 10% of an occlusive agent component by weight of the formulation;

from about 4% to about 7% of a stiffening agent component by weight of the formulation;

from about 7% to about 13% of an emollient component by weight of the formulation;

from about 4% to about 7% of an emulsifier component by weight of the formulation;

from about 0.3% to about 0.5% of a stabilizing agent component by weight of the formulation;

from about 20% to about 25% of a solvent component by weight of the formulation; and from about 0.5% to about 1.5% of (R)-3-cyclopentyl-3-[4-(7H-pyrrolo[2,3-d]pyrimidin-4-yl)-1H-pyrazol-1-yl]propanenitrile, or a pharmaceutically acceptable salt thereof, by weight of the formulation on a free base basis.

In some embodiments, the pharmaceutical formulation comprises:

from about 45% to about 55% of water by weight of the formulation;

about 7% of an occlusive agent component by weight of the formulation;

from about 4.5% to about 5% of a stiffening agent component by weight of the formulation;

about 10% of an emollient component by weight of the formulation;

from about 4% to about 4.5% of an emulsifier component by weight of the formulation;

about 0.4% of a stabilizing agent component by weight of the formulation;

about 22% of a solvent component by weight of the formulation; and from about 0.5% to about 1.5% of (R)-3-cyclopentyl-3-[4-(7H-pyrrolo[2,3-d]pyrimidin-4-yl)-1H-pyrazol-1-yl]propanenitrile, or a pharmaceutically acceptable salt thereof, by weight of the formulation on a free base basis.

In some embodiments, the combined amount of the stiffening agent component and the emulsifier component is at least about 8% by weight of the formulation.

In some embodiments:

the occlusive agent component comprises a petrolatum;

the stiffening agent component comprises one or more substances independently selected from one or more fatty alcohols;

the emollient component comprises one or more substances independently selected from mineral oils and triglycerides;

the emulsifier component comprises one or more substances independently selected from glyceryl fatty esters and sorbitan fatty esters;

the stabilizing agent component comprises one or more substances independently selected from polysaccharides; and the solvent component comprises one or more substances independently selected from alkylene glycols and polyalkylene glycols.

In some embodiments:

the occlusive agent component comprises white petrolatum;

the stiffening agent component comprises one or more substances independently selected from cetyl alcohol and stearyl alcohol;

the emollient component comprises one or more substances independently selected from light mineral oil, medium chain triglycerides, and dimethicone;

the emulsifier component comprises one or more substances independently selected from glyceryl stearate and polysorbate 20;

the stabilizing agent component comprises xanthan gum; and the solvent component comprises one or more substances independently selected from propylene glycol and polyethylene glycol.

In some embodiments, the pharmaceutical formulation further comprises an antimicrobial preservative component.

In some embodiments, the antimicrobial preservative component is present in an amount of about 0.05% to about 3% by weight of the formulation.

In some embodiments, the antimicrobial preservative component is present in an amount of about 0.1% to about 1% by weight of the formulation.

As used herein, the phrase "antimicrobial preservative component" is a substance or mixtures of substances which inhibits microbial growth in the formulation.

In some embodiments, the antimicrobial preservative component comprises one or more substances independently selected from alkyl parabens and phenoxyethanol.

In some embodiments, the antimicrobial preservative component comprises one or more substances independently selected from methyl paraben, propyl paraben, and phenoxyethanol.

In some embodiments, the pharmaceutical formulation further comprises a chelating agent component.

As used herein, the phrase "chelating agent component" refers to a compound or mixtures of compounds that has the ability to bind strongly with metal ions.

In some embodiments, the chelating agent component comprises edetate disodium.

(R)-3-(4-(7H-Pyrrolo[2,3-d]pyrimidin-4-yl)-1H-pyrazol-1-yl)-3-cyclopentylpropanenitrile can be prepared as described in U.S. Pat. No. 7,598,257 and U.S. Patent Publ. No. 2009/0181959, each of which is incorporated herein by reference in its entirety. The 1:1 phosphate salt of (R)-3-(4-(7H-pyrrolo[2,3-d]pyrimidin-4-yl)-1H-pyrazol-1-yl)-3-cyclopentylpropanenitrile can be prepared as described in U.S. Patent Publ. No. 2008/0312259, which is incorporated herein by reference in its entirety.

The compounds of the present invention also include pharmaceutically acceptable salts of the compounds disclosed herein. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient. Pharmaceutically acceptable salts, including mono- and bi-salts, include, but are not limited to, those derived from organic and inorganic acids such as, but not limited to, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids. Lists of suitable salts are found in Remington's *Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in their entireties.

It will also be understood that compounds described herein may exist in solvated, for example hydrated, as well as unsolvated forms. It will further be understood that the present invention encompasses all such solvated forms of the compounds.

As used herein, "% by weight of the formulation" means the percent concentration of the component in the formulation is on weight/weight basis. For example, 1% w/w of component A=[(mass of component A)/(total mass of the formulation)]×100.

As used herein, "% by weight of the formulation on a free base basis" of (R)-3-(4-(7H-pyrrolo[2,3-d]pyrimidin-4-yl)-1H-pyrazol-1-yl)-3-cyclopentylpropanenitrile, or pharmaceutically acceptable salt thereof" means that the % w/w is calculated based on the weight of (R)-3-(4-(7H-pyrrolo[2,3-d]pyrimidin-4-yl)-1H-pyrazol-1-yl)-3-cyclopentylpropanenitrile in the total formulation. For example, "0.5% w/w on a free base basis" of (R)-3-(4-(7H-pyrrolo[2,3-d]pyrimidin-4-yl)-1H-pyrazol-1-yl)-3-cyclopentylpropanenitrile phosphate means that for 100 grams of total formulation, there are 0.66 grams of (R)-3-(4-(7H-pyrrolo[2,3-d]pyrimidin-4-yl)-1H-pyrazol-1-yl)-3-cyclopentylpropanenitrile phosphate in the formulation (which equates to 0.5 grams of the free base, (R)-3-(4-(7H-pyrrolo[2,3-d]pyrimidin-4-yl)-1H-pyrazol-1-yl)-3-cyclopentylpropanenitrile).

In some embodiments, the components are present in exactly the ranges specified (e.g., the term "about" is not present). In some embodiments, "about" means plus or minus 10% of the value.

As will be appreciated, some components of the pharmaceutical formulations described herein can possess multiple functions. For example, a given substance may act as both an emulsifying agent component and a stabilizing agent. In some such cases, the function of a given component can be considered singular, even though its properties may allow multiple functionality. In some embodiments, each component of the formulation comprises a different substance or mixture of substances.

As used herein, the term "component" can mean one substance or a mixture of substances.

As used herein, the term "fatty acid" refers to an aliphatic acid that is saturated or unsaturated. In some embodiments, the fatty acid is in a mixture of different fatty acids. In some embodiments, the fatty acid has between about eight to about thirty carbons on average. In some embodiments, the fatty acid has about 12 to 20, 14-20, or 16-18 carbons on average. Suitable fatty acids include, but are not limited to, cetyl acid, stearic acid, lauric acid, myristic acid, erucic acid, palmitic acid, palmitoleic acid, capric acid, caprylic acid, oleic acid, linoleic acid, linolenic acid, hydroxystearic acid, 12-hydroxystearic acid, cetostearic acid, isostearic acid, sesquioleic acid, sesqui-9-octadecanoic acid, sesquiisooctadecanoic acid, behenic acid, isobehenic acid, and arachidonic acid, or mixtures thereof.

As used herein, the term "fatty alcohol" refers to an aliphatic alcohol that is saturated or unsaturated. In some embodiments, the fatty alcohol is in a mixture of different fatty alcohols. In some embodiments, the fatty alcohol has between about 12 to about 20, about 14 to about 20, or about 16 to about 18 carbons on average. Suitable fatty alcohols include, but are not limited to, stearyl alcohol, lauryl alcohol, palmityl alcohol, cetyl alcohol, capryl alcohol, caprylyl alcohol, oleyl alcohol, linolenyl alcohol, arachidonic alcohol, behenyl alcohol, isobehenyl alcohol, selachyl alcohol, chimyl alcohol, and linoleyl alcohol, or mixtures thereof.

As used herein, the term "polyalkylene glycol", employed alone or in combination with other terms, refers to a polymer containing oxyalkylene monomer units, or copolymer of different oxyalkylene monomer units, wherein the alkylene group has 2 to 6, 2 to 4, or 2 to 3 carbon atoms. As used herein, the term "oxyalkylene", employed alone or in combination with other terms, refers to a group of formula —O— alkylene-. In some embodiments, the polyalkylene glycol is polyethylene glycol.

As used herein, the term, "sorbitan fatty ester" includes products derived from sorbitan or sorbitol and fatty acids and, optionally, poly(ethylene glycol) units, including sorbitan esters and polyethoxylated sorbitan esters. In some embodiments, the sorbitan fatty ester is a polyethoxylated sorbitan ester.

As used herein, the term "sorbitan ester" refers to a compound, or mixture of compounds, derived from the esterification of sorbitol and at least one fatty acid. Fatty acids useful for deriving the sorbitan esters include, but are not limited to, those described herein. Suitable sorbitan esters include, but are not limited to, the Span™ series (available from Uniqema), which includes Span 20 (sorbitan monolaurate), 40 (sorbitan monopalmitate), 60 (sorbitan monostearate), 65 (sorbitan tristearate), 80 (sorbitan monooleate), and 85 (sorbitan trioleate). Other suitable sorbitan esters include those listed in R. C. Rowe and P. J. Shesky, Handbook of pharmaceutical excipients, (2006), 5th ed., which is incorporated herein by reference in its entirety.

As used herein, the term "polyethoxylated sorbitan ester" refers to a compound, or mixture thereof, derived from the ethoxylation of a sorbitan ester. The polyoxethylene portion of the compound can be between the fatty ester and the sorbitan moiety. As used herein, the term "sorbitan ester" refers to a compound, or mixture of compounds, derived from the esterification of sorbitol and at least one fatty acid. Fatty acids useful for deriving the polyethoyxlated sorbitan esters include, but are not limited to, those described herein. In some embodiments, the polyoxyethylene portion of the compound or mixture has about 2 to about 200 oxyethylene units. In some embodiments, the polyoxyethylene portion of the compound or mixture has about 2 to about 100 oxyethylene units. In some embodiments, the polyoxyethylene portion of the compound or mixture has about 4 to about 80 oxyethylene units. In some embodiments, the polyoxyethylene portion of the compound or mixture has about 4 to about 40 oxyethylene units. In some embodiments, the polyoxyethylene portion of the compound or mixture has about 4 to about 20 oxyethylene units. Suitable polyethoxylated sorbitan esters include, but are not limited to the Tween™ series (available from Uniqema), which includes Tween 20 (POE(20) sorbitan monolaurate), 21 (POE(4) sorbitan monolaurate), (POE(20) sorbitan monopalmitate), 60 (POE(20) sorbitan monostearate), 60K (POE(20) sorbitan monostearate), 61 (POE(4) sorbitan monostearate), 65 (POE(20) sorbitan tristearate), 80 (POE(20) sorbitan monooleate), 80K (POE(20) sorbitan monooleate), 81 (POE (5) sorbitan monooleate), and 85 (POE(20) sorbitan trioleate). As used herein, the abbreviation "POE" refers to polyoxyethylene. The number following the POE abbreviation refers to the number of oxyethylene repeat units in the compound. Other suitable polyethoxylated sorbitan esters include the polyoxyethylene sorbitan fatty acid esters listed in R. C. Rowe and P. J. Shesky, Handbook of pharmaceutical excipients, (2006), 5th ed., which is incorporated herein by reference in its entirety. In some embodiments, the polyethoxylated sorbitan ester is a polysorbate. In some embodiments, the polyethoxylated sorbitan ester is polysorbate 20.

As used herein, the term "glyceryl fatty esters" refers to mono-, di- or triglycerides of fatty acids. The glyceryl fatty esters may be optionally substituted with sulfonic acid groups, or pharmaceutically acceptable salts thereof. Suitable fatty acids for deriving glycerides of fatty acids include, but are not limited to, those described herein. In some embodiments, the glyceryl fatty ester is a mono-glyceride of a fatty acid having 12 to 18 carbon atoms. In some embodiments, the glyceryl fatty ester is glyceryl stearate.

As used herein, the term "triglycerides" refers to a triglyceride of a fatty acid. In some embodiments, the triglyceride is medium chain triglycerides.

As used herein, the term "alkylene glycol" refers to a group of formula —O— alkylene-, wherein the alkylene group has 2 to 6, 2 to 4, or 2 to 3 carbon atoms. In some embodiments, the alkylene glycol is propylene glycol (1,2-propanediol).

As used herein, the term "polyethylene glycol" refers to a polymer containing ethylene glycol monomer units of formula $—O—CH_2—CH_2—$. Suitable polyethylene glycols may have a free hydroxyl group at each end of the polymer molecule, or may have one or more hydroxyl groups etherified with a lower alkyl, e.g., a methyl group. Also suitable are derivatives of polyethylene glycols having esterifiable carboxy groups. Polyethylene glycols useful in the present invention can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to polyethylene glycol-200, polyethylene glycol-300, polyethylene glycol-400, polyethylene glycol-600, and polyethylene glycol-900. The number following the dash in the name refers to the average molecular weight of the polymer.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Methods

The pharmaceutical formulations of the invention are useful in treating skin disorders. In some embodiments, the skin disorder is an autoimmune bullous skin disorder such as pemphigus vulgaris (PV) or bullous pemphigoid (BP). In some embodiments, the skin disorder is psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, co-administration or sequential administration of the topical formulations of the invention together with the agent causing unwanted sensitization can be helpful in treating such unwanted sensitization or dermatitis.

The present invention further provides a method of treating dermatological side effects of other pharmaceuticals by administration of the compound of the invention. For example, numerous pharmaceutical agents result in unwanted allergic reactions which can manifest as acneiform rash or related dermatitis. Example pharmaceutical agents that have such undesirable side effects include anticancer drugs such as gefitinib, cetuximab, erlotinib, and the like. The formulations of the invention can be administered systemically or topically (e.g., localized to the vicinity of the dermatitis) in combination with (e.g., simultaneously or sequentially) the pharmaceutical agent having the undesirable dermatological side effect. In some embodiments, the formulation of the invention can be administered topically together with one or more other pharmaceuticals, where the other pharmaceuticals when topically applied in the absence of a formulation of the invention cause contact dermatitis, allergic contact sensitization, or similar skin disorder. Accordingly, formulation of the invention include topical formulations further comprising an additional pharmaceutical agent which can cause dermatitis, skin disorders, or related side effects.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

One or more additional pharmaceutical agents such as, for example, chemotherapeutics, anti-inflammatory agents, steroids, immunosuppressants, as well as Bcr-Abl, Flt-3, RAF and FAK kinase inhibitors such as, for example, those described in WO 2006/056399, or other agents can be used in combination with the formulations of the present invention for treatment of JAK-associated diseases, disorders or conditions. The one or more additional pharmaceutical agents can be administered to a patient simultaneously or sequentially.

Example chemotherapeutic include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, the formulations of the invention can be used in combination with one or more other kinase inhibitors including imatinib, particularly for treating patients resistant to imatinib or other kinase inhibitors.

In some embodiments, a corticosteroid such as dexamethasone is administered to a patient in combination with the compound of the invention where the dexamethasone is administered intermittently as opposed to continuously.

Labeled Compounds and Assay Methods

Another aspect of the present invention relates to formulations comprising a labeled active compound (radio-labeled, fluorescent-labeled, etc.) that would be useful not only in imaging techniques but also in assays, both in vitro and in vivo, for localizing and quantitating JAK in tissue samples, including human, and for identifying JAK ligands by inhibition binding of a labeled compound. Accordingly, the present invention includes JAK assays that contain such labeled compounds.

The present invention further includes formulations of an isotopically-labeled compound. An "isotopically" or "radio-labeled" compound is a compound where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{15}S$, $^{36}Cl$, $^{82}Br$, $^{75}Br$, $^{76}Br$, $^{77}Br$, $^{123}I$, $^{124}$, $^{125}I$ and $^{131}I$. The radionuclide that is incorporated in the instant radio-labeled compounds will depend on the specific application of that radio-labeled compound. For example, for in vitro JAK labeling and competition assays, compounds that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}Br$.

Kits

The present invention also includes pharmaceutical kits useful, for example, in the treatment or prevention of JAK-associated diseases or disorders, such as cancer, which include one or more containers containing a pharmaceutical formulation of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. In some embodiments, the present invention provides pharmaceutical formulations comprising the components specified in the example formulations (e.g., Example 3), wherein the components are present in about the amounts in Tables 2-5.

EXAMPLES

Example 1: (3R)- and (3S)-3-Cyclopentyl-3-[4-(7H-pyrrolo[2,3-d]pyrimidin-4-yl)-1H-pyrazol-1-yl]propanenitrile

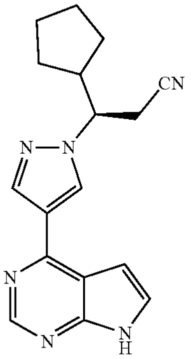

and

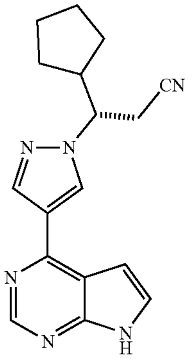

Step 1. (2E)- and (2Z)-3-Cyclopentylacrylonitrile

To a solution of 1.0 M potassium tert-butoxide in THE (235 mL) at 0° C. was added dropwise a solution of diethyl cyanomethylphosphonate (39.9 mL, 0.246 mol) in THF (300 mL). The cold bath was removed and the reaction was warmed to room temperature followed by recooling to 0° C., at which time a solution of cyclopentanecarbaldehyde (22.0 g, 0.224 mol) in THE (60 mL) was added dropwise. The bath was removed and the reaction warmed to ambient temperature and stirred for 64 hours. The mixture was partitioned between diethyl ether and water, the aqueous was extracted with three portions of ether, followed by two portions of ethyl acetate. The combined extracts were washed with brine, then dried over sodium sulfate, filtered and concentrated in vacuo to afford a mixture containing 24.4 g of olefin isomers which was used without further purification (89%).

$^{1}H$ NMR (400 MHz, $CDCl_3$): δ 6.69 (dd, 1H, trans olefin), 6.37 (t, 1H, cis olefin), 5.29 (dd, 1H, trans olefin), 5.20 (d, 1H, cis olefin), 3.07-2.95 (m, 1H, cis product), 2.64-2.52 (m, 1H, trans product), 1.98-1.26 (m, 16H).

Step 2. (3R)- and (3S)-3-Cyclopentyl-3-[4-(7-[2-(trimethylsilyl)ethoxy]methyl-7H-pyrrolo[2,3-d]pyrimidin-4-yl)-1H-pyrazol-1-yl]propanenitrile To a solution of 4-(1H-pyrazol-4-yl)-7-[2-(trimethylsilyl)ethoxy]methyl-7H-pyrrolo[2,3-d]pyrimidine (15.0 g, 0.0476 mol) in ACN (300 mL) was added 3-cyclopentylacrylonitrile (15 g, 0.12 mol) (as a mixture of cis and trans isomers), followed by DBU (15 mL, 0.10 mol). The resulting mixture was stirred at room temperature overnight. The ACN was evaporated. The mixture was diluted with ethyl acetate, and the solution was washed with 1.0 N HCl. The aqueous layer was back-extracted with three portions of ethyl acetate. The combined organic extracts were washed with brine, dried over sodium sulfate, filtered and concentrated. The crude product was purified by silica gel chromatography (gradient of ethyl acetate/hexanes) to yield a viscous clear syrup, which was dissolved in ethanol and evaporated several times to remove ethyl acetate, to afford 19.4 g of racemic adduct (93%). The enantiomers were separated by preparative-HPLC, (OD-H, 15% ethanol/hexanes) and used separately in the next step to generate their corresponding final product. The final products (see Step 3) stemming from each of the separated enantiomers were found to be active JAK inhibitors; however, the final product stemming from the second peak to elute from the preparative-HPLC was more active than its enantiomer.

$^1$H NMR (300 MHz, $CDCl_3$): δ 8.85 (s, 1H), 8.32 (s, 2H), 7.39 (d, 1H), 6.80 (d, 1H), 5.68 (s, 2H), 4.26 (dt, 1H), 3.54 (t, 2H), 3.14 (dd, 1H), 2.95 (dd, 1H), 2.67-2.50 (m, 1H), 2.03-1.88 (m, 1H), 1.80-1.15 (m, 7H), 0.92 (t, 2H), −0.06 (s, 9H); MS(ES): 437 (M+1).

Step 3. (3R)- and (3S)-3-Cyclopentyl-3-[4-(7H-pyrrolo[2,3-d]pyrimidin-4-yl)-1H-pyrazol-1-yl]propanenitrile To a solution of 3-cyclopentyl-3-[4-(7-[2-(trimethylsilyl)ethoxy]methyl-7H-pyrrolo[2,3-d]pyrimidin-4-yl)-1H-pyrazol-1-yl]propanenitrile (6.5 g, 0.015 mol, R or S enantiomer as isolated above) in DCM (40 mL) was added TFA (16 mL) and this was stirred for 6 hours. The solvent and TFA were removed in vacuo. The residue was dissolved in DCM and concentrated using a rotary evaporator two further times to remove as much as possible of the TFA. Following this, the residue was stirred with ethylenediamine (4 mL, 0.06 mol) in methanol (30 mL) overnight. The solvent was removed in vacuo, water was added and the product was extracted into three portions of ethyl acetate. The combined extracts were washed with brine, dried over sodium sulfate, decanted and concentrated to afford the crude product which was purified by flash column chromatography (eluting with a gradient of methanol/DCM). The resulting mixture was further purified by preparative-HPLC/MS (C18 eluting with a gradient of $ACN/H_2O$ containing 0.15% $NH_4OH$) to afford product (2.68 g, 58%).

$^1$H NMR (400 MHz, $D_6$-dmso): δ 12.11 (br s, 1H), 8.80 (s, 1H), 8.67 (s, 1H), 8.37 (s, 1H), 7.60 (d, 1H), 6.98 (d, 1H), 4.53 (dt, 1H), 3.27 (dd, 1H), 3.19 (dd, 1H), 2.48-2.36 (m, 1H), 1.86-1.76 (m, 1H), 1.68-1.13 (m, 7H); MS(ES): 307 (M+1).

Example 2: (R)-3-(4-(7H-pyrrolo[2,3-d]pyrimidin-4-yl)-1H-pyrazol-1-yl)-3-cyclopentylpropanenitrile phosphoric acid salt

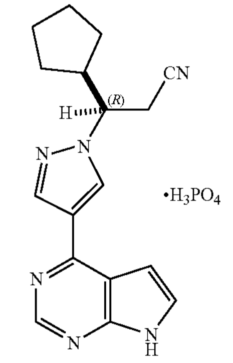

To a test tube was added (R)-3-(4-(7H-pyrrolo[2,3-d]pyrimidin-4-yl)-1H-pyrazol-1-yl)-3-cyclopentylpropanenitrile (153.5 mg) and phosphoric acid (56.6 mg) followed by isopropyl alcohol (IPA) (5.75 mL). The resulting mixture was heated to clear, cooled to room temperature, and then stirred for another 2 hours. The precipitate was collected by filtration and the cake was washed with 0.6 mL of cold IPA. The cake was dried under vacuum to constant weight to provide the final salt product (171.7 mg).

The phosphoric acid salt was shown to be a 1:1 salt by $^1$H NMR and crystallinity was confirmed by X-ray powder diffraction (XRPD). Differential scanning calorimetry (DSC) gave a sharp melting peak at about 198.66° C. The product showed little weight loss up to 200° C. by TGA.

Example 3: Preparation of Oil-In-Water Cream Formulations of (R)-3-(4-(7H-pyrrolo[2,3-d]pyrimidin-4-yl)-1H-pyrazol-1-yl)-3-cyclopentylpropanenitrile phosphoric acid salt An oil-in-water cream formulation was prepared for (R)-3-(4-(7H-pyrrolo[2,3-d]pyrimidin-4-yl)-1H-pyrazol-1-yl)-3-cyclopentylpropanenitrile phosphoric acid salt (Example 2) at 0.5, 1.0 and 1.5% by weight of the formulation (free base equivalent). The compositions for a 15 gram tube are provided in Table 2 below. The formulation for three strengths were identical except for adjustments to the purified water quantity based on the amount of active ingredient. All excipients used in the formulation were compendial grade (ie, USP/NF or BP) or are approved for use in topical products.

The quantitative formulae for representative 400 kg batches of the cream formulation for Example 2 at 0.5, 1.0 and 1.5% are also provided in Tables 3, 4, and 5, respectively.

TABLE 2

| FORMULA | | | Percentage of Total | |
|---|---|---|---|---|
| PHASE | COMPONENT | Function | (% w/w) | Grams/Tube |
| Paraben | Propylene Glycol USP | Solvent | 10.00 | 1.5 |
| | Methyl Paraben NF | Antimicrobial preservative | 0.10 | 0.015 |
| | Propyl Paraben NF | Antimicrobial preservative | 0.05 | 0.0075 |

TABLE 2-continued

| FORMULA | | | Percentage of Total | |
|---|---|---|---|---|
| PHASE | COMPONENT | Function | (% w/w) | Grams/Tube |
| Xanthan Gum | Propylene Glycol USP | Solvent | 5.00 | 0.75 |
| | Xanthan Gum NF | Suspending, stabilizing, viscosity-increasing agent | 0.40 | 0.06 |
| Oil | Light Mineral Oil NF | Emollient, solvent | 4.00 | 0.6 |
| | Glyceryl Stearate SE | Emulsifier | 3.00 | 0.45 |
| | Polysorbate 20 NF | Emulsifying/stabilizing agent | 1.25 | 0.1875 |
| | White Petrolatum USP | Occlusive agent | 7.00 | 1.05 |
| | Cetyl Alcohol NF | Stiffening agent, consistency improver | 3.00 | 0.45 |
| | Stearyl Alcohol NF | Stiffening agent | 1.75 | 0.2625 |
| | Dimethicone 360 NF | Skin protectant | 1.00 | 0.15 |
| | Medium Chain Triglyceride NF | Emollient, solvent | 5.00 | 0.75 |
| Aqueous/Active | Purified Water USP | Solvent | 50.24-48.92 | 7.536-7.338 |
| | Edetate Disodium USP | Chelating agent | 0.05 | 0.0075 |
| | Polyethylene Glycol USP | Solvent | 7.00 | 1.05 |
| | Example 2 * | Active | 0.66-1.98 | 0.099-0.297 |
| Final | Phenoxyethanol BP | Antimicrobial preservative | 0.50 | 0.075 |
| | Total | | 100.00% | 15 |

* 1.32% of Example 2 is equivalent to 1.0% of (R)-3-(4-(7H-pyrrolo[2,3-d]pyrimidin-4-yl)-1H-pyrazol-1-yl)-3-cyclopentyl-propanenitrile free base

TABLE 3

| Ingredient | Kilograms | Percentage (w/w) |
|---|---|---|
| (R)-3-(4-(7H-pyrrolo[2,3-d]pyrimidin-4-yl)-1H-pyrazol-1-yl)-3-cyclopentylpropanenitrile phosphoric acid salt (Example 2) | 2.64 (phosphate salt)/ 2.0 (free base) | 0.66 (phosphate salt)/ 0.5 (free base) |
| Propylene Glycol USP | 40.0 | 10.00 |
| Methyl Paraben NF | 0.4 | 0.10 |
| Propyl Paraben NF | 0.2 | 0.05 |
| Propylene Glycol USP | 20.0 | 5.00 |
| Xanthan Gum NF | 1.6 | 0.40 |
| Light Mineral Oil NF | 16.0 | 4.00 |
| Glyceryl Stearate SE | 12.0 | 3.00 |
| Polysorbate 20 NF | 5.0 | 1.25 |
| White Petrolatum USP | 28.0 | 7.00 |
| Cetyl alcohol NF | 12.0 | 3.00 |
| Stearyl alcohol NF | 7.0 | 1.75 |
| Dimethicone 360 NF | 4.0 | 1.00 |
| Medium Chain Triglycerides NF | 20.0 | 5.00 |
| Purified Water USP (approximate) | 201 | 50.25 |
| Edetate Disodium USP | 0.2 | 0.05 |
| Polyethylene Glycol USP | 28.0 | 7.00 |
| Phenoxyethanol BP | 2.0 | 0.5 |
| Total (approximate) | 400.0 | 100 |

TABLE 4

| Ingredient | Kilograms | Percentage (w/w) |
|---|---|---|
| (R)-3-(4-(7H-pyrrolo[2,3-d]pyrimidin-4-yl)-1H-pyrazol-1-yl)-3-cyclopentylpropanenitrile phosphoric acid salt (Example 2) | 5.28 (phosphate salt)/ 4.0 (free base) | 1.32 (phosphate salt)/ 1.00 (fre ebase) |

TABLE 4-continued

| Ingredient | Kilograms | Percentage (w/w) |
|---|---|---|
| Propylene Glycol USP | 40.0 | 10.00 |
| Methyl Paraben NF | 0.4 | 0.10 |
| Propyl Paraben NF | 0.2 | 0.05 |
| Propylene Glycol USP | 20.0 | 5.00 |
| Xanthan Gum NF | 1.6 | 0.40 |
| Light Mineral Oil NF | 16.0 | 4.00 |
| Glyceryl Stearate SE | 12.0 | 3.00 |
| Polysorbate 20 NF | 5.0 | 1.25 |
| White Petrolatum USP | 28.0 | 7.00 |
| Cetyl alcohol NF | 12.0 | 3.00 |
| Stearyl alcohol NF | 7.0 | 1.75 |
| Dimethicone 360 NF | 4.0 | 1.00 |
| Medium Chain Triglycerides NF | 20.0 | 5.00 |
| Purified Water USP (approximate) | 198.5 | 49.6 |
| Edetate Disodium USP | 0.2 | 0.05 |
| Polyethylene Glycol USP | 28.0 | 7.00 |
| Phenoxyethanol BP | 2.0 | 0.5 |
| Total (approximate) | 400.0 | 100 |

TABLE 5

| Ingredient | Kilograms | Percentage (w/w) |
|---|---|---|
| (R)-3-(4-(7H-pyrrolo[2.3-d]pyrimidin-4-yl)-1H-pyrazol-1-yl)-3-cyclopentylpropanenitrile phosphoric acid salt (Example 2) | 7.92 (phosphate salt)/ 6.0 (free base) | 1.98 (phophate salt)/ 1.5 (free base) |
| Propylene Glycol USP | 40.0 | 10.00 |
| Methyl Paraben NF | 0.4 | 0.10 |
| Propyl Paraben NF | 0.2 | 0.05 |
| Propylene Glycol USP | 20.0 | 5.00 |
| Xanthan Gum NF | 1.6 | 0.40 |
| Light Mineral Oil NF | 16.0 | 4.00 |
| Glyceryl Stearate SE | 12.0 | 3.00 |
| Polysorbate 20 NF | 5.0 | 1.25 |
| White Petrolatum USP | 28.0 | 7.00 |
| Cetyl alcohol NF | 12.0 | 3.00 |
| Stearyl alcohol NF | 7.0 | 1.75 |
| Dimethicone 360 NF | 4.0 | 1.00 |
| Medium Chain Triglycerides NF | 20.0 | 5.00 |
| Purified Water USP (approximate) | 195.5 | 48.9 |
| Edetate Disodium USP | 0.2 | 0.05 |
| Polyethylene Glycol USP | 28.0 | 7.00 |
| Phenoxyethanol BP | 2.0 | 0.5 |
| Total (approximate) | 400.0 | 100 |

The oil-in-water cream formulations were synthesized according to the following procedure at either a 3.5 kg or 400 kg scale (when made at a 3.5 kg batch size, the amounts in Tables 3-5 were scaled appropriately). Some batches were subject to minor changes associated with scale-up, such as the size of mixing vessels and mixers. Generally, overhead mixer with high and low shear mixing blades are suitable for the process. FIG. 1 shows a flowchart representation of the process for making the oil-in-water formulation. The (R)-3-(4-(7H-pyrrolo[2,3-d]pyrimidin-4-yl)-1H1-pyrazol-1-yl)-3-cyclopentyipropanenitrile is referred to as "API" throughout this application.

Procedure

1. A paraben phase was prepared by mixing methyl and propyl parabens with a portion of the propylene glycol (see % in Tables 2-5).
2. Next, a xanthan gum phase was prepared by mixing xanthan gum with propylene glycol (see % in Table 2-5).
3. An oil phase was then prepared by mixing light mineral oil, glyceryl stearate, polysorbate 20, white petrolatum, cetyl alcohol, stearyl alcohol, dimethicone and medium chain triglycerides. The phase is heated to 70-80° C. to melt and form a uniform mixture.
4. The aqueous phase was next prepared by mixing purified water, polyethylene glycol, and disodium EDTA. The phase is heated to 70-80° C.
5. The aqueous phase of step 4, paraben phase of step 1, and Example 2 (phosphate salt of API) were combined to form a mixture.
6. The xanthan gum phase from step 2 was then added to the mixture from step 5.
7. The oil phase from step 3 was then combined under high shear mixing with the mixture from step 6 to form an emulsion.
8. Phenoxyethanol was then added to the emulsion from step 7. Mixing was continued, and then the product was cooled under low shear mixing.

More consistent batches at larger scales (e.g., 140 kg) could be obtained by adding Example 2 gradually to the aqueous phase and then combining with the other phases. Similarly, more consistent batches could be obtained by slower cooling (e.g., by using room temperature water in the outer jacket of the reactor, rather than lower temperature water.

Analytical Results for Cream Formulations and Stability Studies

A. Methods

The appearance of the cream was visually inspected. Viscosity was measured using a Brookfield viscometer at 25° C. The pH was measured on the final cream formulation. The microbial limit testing is performed as per USP. The fill weight is analyzed as an in-process test during filling of the cream into tubes.

Assay, related substances, identity and content uniformity were determined in the formulation by a gradient reverse-phase HPLC with UV detection at 294 nm. A Waters HPLC was used with a Zorbax SB-C18 column (3.5 μm, 4.6×150 mm) at a flow rate of 1.0 mL/minute, temperature of 40° C. using Mobile Phase A of 2 mL of TFA into 4 L of Water (0.05% TFA), or Mobile Phase B of 2 mL of TFA into 4 L of methanol (0.05% TFA).

B. Results

Results are shown below for a 3.5 kg batches at 0.5%, 1% and 1.5% strength of Example 2 (free base basis (API)) (Table 6).

TABLE 6

| Test | Acceptance Criteria | Strength | | | | |
|---|---|---|---|---|---|---|
| | | Placebo | | 0.5% w/w | 1.0% w/w | 1.5% w/w |
| Appearance | Smooth, white emulsion | Conforms | | Conforms | Conforms | Conforms |
| pH | Report results | 6.5 | | 3.6 | 3.3 | 3.1 |
| Viscosity | Report results | 96,500 | | 66,500 | 64,800 | 72,900 |
| API Assay (%) | 90.0-110.0% | N/A | | 100.0 | 102.0 | 102.0 |
| API Related Substances | Report results | ND* | | ND* | ND* | ND* |
| Content Uniformity testing | 90-110% RSD: ≤5% | Top | N/A | 100 | 101 | 101 |
| | | | | 100 | 101 | 101 |
| | | Middle | N/A | 100 | 101 | 102 |
| | | | | 100 | 102 | 103 |
| | | Bottom | N/A | 100 | 102 | 103 |
| | | | | 100 | 102 | 102 |
| | | Avg. | N/A | 100 | 102 | 102 |
| | | RSD % | | 0.0 | 0.5 | 0.8 |

The stability data from batches of the cream formulation at 0.5, 1.0 and 1.5% w/w strength stored in 15 gram aluminum tubes is provided in Tables 7-10 and 19-20. Further, stability data from batches of the cream formulation at 0.5, 1.0 and 1.5% w/w strength packaged in amber glass jars (2 oz. with teflon cap) is provided in Tables 13-17, while longer stability data for the 1.0% w/w formulation packaged in 16 oz. amber glass jars is provided in Tables 11-12. The preliminary stability data for the drug product did not show any chemical instability after 3 months of storage at 25° C./60% RH and 40° C./75% RH in either packaging configuration. A change in viscosity is seen following 3 months at 40° C./75% RH for formulation stored in amber glass jars. However, physical inspection of the product did not indicate any phase separation.

Acceptance criteria are shown below.

| Test | Acceptance Criteria |
|---|---|
| Appearance | Smooth, white cream |
| pH | Report results |
| Weight Loss | Report results |
| Viscosity (cps) | Report results |
| API Assay (%) | 90.0-110.0% of label claim |
| API Related Substances (RRT:Area %) | Report results |
| Total Related Substances (RRT:Area %) | Report results |
| MLT (Objectionable organisms) | Absent/1 g |
| MLT (*P. Aeruginosa*) | Absent/1 g |
| MLT (*S. Aureus*) | Absent/1 g |
| MLT (Total Aerobic) | NMT 100 CFU/g |
| MLT (Total Yeast and Molds) | NMT 10 CFU/g |

TABLE 7

Stability Data for 0.5% w/w Cream at 25° C./60% RH (15 aluminum gram tubes)

| Test | Time (Months) 0 | 1 | 3 | 6 |
|---|---|---|---|---|
| Appearance | Conforms | Conforms | Conforms | Conforms |
| pH | 3.6 | 3.6 | 3.6 | 3.6 |
| Weight Loss | NA | NA | 0.0 | 0.0 |
| Viscosity (cps) | 23400 | 29900 | 25400 | 24900 |
| API Assay (%) | 103.7 | 107.2 | 102.5 | 105.9 |
| API Related Substances (RRT:Area %) | ND | ND | 1.09:0.15<br>1.18:0.19 | ND |
| Total Related Substances (RRT:Area %) | NA | NA | 0.34 | NA |
| MLT (Objectionable organisms) | Absent/1 g | NA | Absent/1 g | Absent/1 g |
| MLT (*P. Aeruginosa*) | Absent/1 g | NA | Absent/1 g | Absent/1 g |
| MLT (*S. Aureus*) | Absent/1 g | NA | Absent/1 g | Absent/1 g |

TABLE 7-continued

Stability Data for 0.5% w/w Cream at 25° C./60% RH (15 aluminum gram tubes)

| | | | | |
|---|---|---|---|---|
| MLT (Total Aerobic) | <10 | NA | <10 | <10 |
| MLT (Total Yeast and Molds) | <10 | NA | <10 | <10 |

| | Time (Months) | | | |
|---|---|---|---|---|
| Test | 9 | 12 | 18 | 24 |
| Appearance | Conforms | Conforms | Conforms | Conforms |
| pH | 3.5 | 3.5 | 3.5 | 3.6 |
| Weight Loss | 0.0 | 0.0 | 0.0 | 0.0 |
| Viscosity (cps) | 26000 | 23000 | 20900 | 22500 |
| API Assay (%) | 105.4 | 105.7 | 104.4 | 104.0 |
| API Related Substances (RRT:Area %) | 1.10:0.10 | 1.09:0.14 | 0.95:0.18<br>1.09:0.20 | 0.11:0.24<br>0.95:0.23<br>1.11:0.08 |
| Total Related Substances (RRT:Area %) | 0.10 | 0.14 | 0.38 | 0.55 |
| MLT (Objectionable organisms) | Absent/1 g | Absent/1 g | NA | Absent/1 g |
| MLT (*P. Aeruginosa*) | Absent/1 g | Absent/1 g | NA | Absent/1 g |
| MLT (*S. Aureus*) | Absent/1 g | Absent/1 g | NA | Absent/1 g |
| MLT (Total Aerobic) | <10 | <10 | NA | <10 |
| MLT (Total Yeast and Molds) | <10 | <10 | NA | <10 |

TABLE 8

Stability Data for 0.5% w/w Cream at 40° C./75% RH (15 aluminum gram tubes)

| | Time (Months) | | | |
|---|---|---|---|---|
| Test | 0 mo. | 1 mo. | 3 mo. | 6 mo. |
| Appearance | Conforms | Conforms | Conforms | Conforms |
| pH | 3.6 | 3.6 | 3.6 | 3.5 |
| Weight Loss | N/A | N/A | 0.0 | 0.0 |
| Viscosity (cps) | 23400 | 26300 | 19800 | 18600 |
| API Assay (%) | 103.7 | 103.1 | 105.3 | 105.0 |
| API Related Substances (RRT:Area %) | N/D | N/D | 1.09:0.14 | 1.32:0.21<br>1.39:0.40 |
| Total Related Substances (RRT:Area %) | N/A | N/A | 0.14 | 0.61 |
| MLT (Objectionable organisms) | Absent/1 g | N/A | Absent/1 g | Absent/1 g |
| MLT (*P. Aeruginosa*) | Absent/1 g | N/A | Absent/1 g | Absent/1 g |
| MLT (*S. Aureus*) | Absent/1 g | N/A | Absent/1 g | Absent/1 g |
| MLT (Total Aerobic) | <10 | N/A | <10 | <10 |
| MLT (Total Yeast and Molds) | <10 | N/A | <10 | <10 |

TABLE 9

Stability Data for 1.5% w/w Cream at 25° C./60% RH (15 aluminum gram tubes)

| | Time (Months) | | | |
|---|---|---|---|---|
| Test | 0 | 1 | 3 | 6 |
| Appearance | Conforms | Conforms | Conforms | Conforms |
| pH | 3.2 | 3.1 | 3.2 | 3.1 |
| Weight Loss | NA | NA | 0.0 | 0.0 |
| Viscosity (cps) | 29433 | 35800 | 27400 | 26200 |
| API Assay (%) | 102.7 | 104.9 | 103.9 | 105.0 |

TABLE 9-continued

Stability Data for 1.5% w/w Cream at 25° C./60% RH (15 aluminum gram tubes)

| | | | | |
|---|---|---|---|---|
| API Related Substances (RRT:Area %) | ND | ND | 1.09:0.14 | ND |
| Total Related Substances (RRT:Area %) | NA | NA | 0.14 | ND |
| MLT (Objectionable organisms) | Absent/1 g | NA | Absent/1 g | Absent/1 g |
| MLT (*P. Aeruginosa*) | Absent/1 g | NA | Absent/1 g | Absent/1 g |
| MLT (*S. Aureus*) | Absent/1 g | NA | Absent/1 g | Absent/1 g |
| MLT (Total Aerobic) | <10 | NA | <10 | <10 |
| MLT (Total Yeast and Molds) | <10 | NA | <10 | <10 |

| | Time (Months) | | | |
|---|---|---|---|---|
| Test | 9 | 12 | 18 | 24 |
| Appearance | Conforms | Conforms | Conforms | Conforms |
| pH | 3.4 | 3.1 | 3.1 | 3.1 |
| Weight Loss | 0.0 | 0.0 | 0.0 | 0.0 |
| Viscosity (cps) | 25600 | 23800 | 21200 | 22200 |
| API Assay (%) | 103.7 | 105.0 | 102.6 | 103.0 |
| API Related Substances (RRT:Area %) | 1.10:0.12 | 1.09:0.13 | 1.09:0.21 | 0.20:0.09<br>0.95:0.07<br>1.11:0.10 |
| Total Related Substances (RRT:Area %) | 0.12 | 0.13 | 0.21 | 0.26 |
| MLT (Objectionable organisms) | Absent/1 g | Absent/1 g | NA | Absent/1 g |
| MLT (*P. Aeruginosa*) | Absent/1 g | Absent/1 g | NA | Absent/1 g |
| MLT (*S. Aureus*) | Absent/1 g | Absent/1 g | NA | Absent/1 g |
| MLT (Total Aerobic) | <10 | <10 | NA | <10 |
| MLT (Total Yeast and Molds) | <10 | <10 | NA | <10 |

TABLE 10

Stability Data for 1.5% w/w Cream at 40° C./75% RH (15 aluminum gram tubes)

| | Time (Months) | | | |
|---|---|---|---|---|
| Test | 0 mo. | 1 mo. | 3 mo. | 6 mo. |
| Appearance | Conforms | Conforms | Conforms | Conforms |
| pH | 3.2 | 3.1 | 3.2 | 3.1 |
| Weight Loss(g) | N/A | N/A | 0.0 | 0.0 |
| Viscosity (cps) | 29433 | 29800 | 22400 | 16300 |
| API Assay | 102.7 | 104.9 | 103.0 | 104.4 |
| API Related Substances RRT:Area % | N/D | N/D | 1.09:0.14 | 1.32:0.20<br>1.39:0.34 |
| Total Related Substance | N/A | N/A | 0.14 | 0.54 |
| Objectionable organisms | Absent/1 g | N/A | Absent/1 g | Absent/1 g |
| *P. Aeruginosa* | Absent/1 g | N/A | Absent/1 g | Absent/1 g |
| *S. Aureus* | Absent/1 g | N/A | Absent/1 g | Absent/1 g |
| Total Aerobic | <10 | N/A | <10 | <10 |
| Total Yeast and Molds | <10 | N/A | <10 | <10 |

TABLE 11

Stability Data for 1.0% w/w Cream at 25° C./60% RH (16 oz. amber glass jars)

| Test | Time (Months) 0 | 3 | 6 | 12 |
|---|---|---|---|---|
| Appearance | Conforms | Conforms | Conforms | Conforms |
| pH | 3.5 | 3.3 | 3.3 | 3.3 |
| Viscosity (cps) | 35700 | 25600 | 21200 | 21400 |
| API Assay | 102.5 | 98.6 | 101.5 | 99.2 |
| API Related Substances (RRT:Area %) | 0.89:0.08 1.15:0.19 | 0.11:0.20 | ND | 0.88:NQ |
| Total Related Substances (RRT:Area %) | 0.27 | 0.20 | NA | 0.20 |
| MLT (Objectionable organisms) | Absent/1 g | Absent/1 g | Absent/1 g | Absent/1 g |
| MLT (*P. Aeruginosa*) | Absent/1 g | Absent/1 g | Absent/1 g | Absent/1 g |
| MLT (*S. Aureus*) | Absent/1 g | Absent/1 g | Absent/1 g | Absent/1 g |
| MLT (Total Aerobic) | <10 | <10 | <10 | <10 |
| MLT (Total Yeast and Molds) | <10 | <10 | <10 | <10 |

NA: Not applicable
ND: Not Detected
NQ: Not Quantifiable

TABLE 12

Stability Data for 1.0% w/w Cream at 25° C./60% RH (16 oz. amber glass jars)

| Test | Time (Months) 0 | 6 |
|---|---|---|
| Appearance | Conforms | Conforms |
| pH | 3.5 | 3.2 |
| API Assay | 102.5 | 100.8 |
| API Related Substances (RRT:Area %) | 0.89:0.08 1.15:0.19 | ND |
| Total Related Substances (RRT:Area %) | 0.27 | ND |
| MLT (Objectionable organisms) | Absent/1 g | Absent/1 g |
| MLT (*P. Aeruginosa*) | Absent/1 g | Absent/1 g |
| MLT (*S. Aureus*) | Absent/1 g | Absent/1 g |
| MLT (Total Aerobic) | <10 | <10 |
| MLT (Total Yeast and Molds) | <10 | <10 |

TABLE 13

Stability Data for 0.5% w/w Cream at 25° C./60% RH (2 oz. amber glass jars)

| Test | Acceptance Criteria | Time (Months) 0 mo. | 1 mo. | 2 mo. | 3 mo. |
|---|---|---|---|---|---|
| Appearance | Smooth, white cream | Conforms | Conforms | Conforms | Conforms |
| pH | Report result | 3.6 | 3.5 | 3.6 | 3.6 |
| Viscosity (cps) | Report results | 66500 | 71500 | 66000 | 56800 |
| API Assay (%) | 90.0-110.0% | 100.0 | 101.0 | 100.0 | 100.0 |
| Related Substances | Report results | ND* | ND* | ND* | ND* |

*Not detected

TABLE 14

Stability Data for 0.5% w/w Cream at 40° C./75% RH (2 oz. amber glass jars)

| Test | Acceptance Criteria | Time (Months) 0 mo. | 1 mo. | 2 mo. | 3 mo. |
|---|---|---|---|---|---|
| Appearance | Smooth, white cream | Conforms | Conforms | Conforms | Conforms |
| pH | Report result | 3.6 | 3.6 | 3.5 | 3.6 |
| Viscosity (cps) | Report results | 66500 | 63900 | 51900 | 39000 |
| API Assay (%) | 90.0-110.0% | 100.0 | 99.0 | 98.0 | 102.0 |
| Related Substances | Report results | ND* | ND* | ND* | ND* |

*Not detected

TABLE 15

| Stability Data for 1.0% w/w Cream at 25° C./60% RH (2 oz. amber glass jars) | | | | | |
|---|---|---|---|---|---|
| | Acceptance | Time (Months) | | | |
| Test | Criteria | 0 mo. | 1 mo. | 2 mo. | 3 mo. |
| Appearance | Smooth, white cream | Conforms | Conforms | Conforms | Conforms |
| pH | Report result | 3.3 | 3.2 | 3.2 | 3.3 |
| Viscosity (cps) | Report results | 64800 | 69300 | 61400 | 50500 |
| API Assay (%) | 90.0-110.0% | 102.0 | 102.0 | 103.0 | 102.5 |
| Related Substances | Report results | ND* | ND* | ND* | ND* |

*Not detected

TABLE 16

| Stability Data for 1.0% w/w Cream at 40° C./75% RH (2 oz. amber glass jars) | | | | | |
|---|---|---|---|---|---|
| | Acceptance | Time (Months) | | | |
| Test | Criteria | 0 mo. | 1 mo. | 2 mo. | 3 mo. |
| Appearance | Smooth, white cream | Conforms | Conforms | Conforms | Conforms |
| pH | Report result | 3.3 | 3.2 | 3.2 | 3.3 |
| Viscosity (cps) | Report results | 64800 | 57900 | 55100 | 33500 |
| API Assay (%) | 90.0-110.0% | 102.0 | 102.0 | 101.0 | 103.0 |
| Related Substances | Report results | ND* | ND* | ND* | ND* |

*Not detected

TABLE 17

| Stability Data for 1.5% w/w Cream at 25° C./60% RH (2 oz. amber glass jars) | | | | | |
|---|---|---|---|---|---|
| | Acceptance | Time (Months) | | | |
| Test | Criteria | 0 mo. | 1 mo. | 2 mo. | 3 mo. |
| Appearance | Smooth, white cream | Conforms | Conforms | Conforms | Conforms |
| pH | Report result | 3.1 | 2.9 | 3.1 | 3.2 |
| Viscosity (cps) | Report results | 72900 | 66600 | 62400 | 60300 |
| API Assay (%) | 90.0-110.0% | 101.7 | 101.7 | 101.7 | 104.3 |
| Related Substances | Report results | ND* | ND* | ND* | ND* |

*Not detected

TABLE 18

| Stability Data for 1.5% w/w Cream at 40° C./75% RH (2 oz. amber glass jars) | | | | | |
|---|---|---|---|---|---|
| | Acceptance | Time (Months) | | | |
| Test | Criteria | 0 mo. | 1 mo. | 2 mo. | 3 mo. |
| Appearance | Smooth, white cream | Conforms | Conforms | Conforms | Conforms |
| pH | Report result | 3.1 | 3.1 | 3.1 | 3.2 |
| Viscosity (cps) | Report results | 72900 | 62500 | 53000 | 43800 |
| Assay (%) | 90.0-110.0% | 101.7 | 103.0 | 102.0 | 104.3 |
| Related Substances | Report results | ND* | ND* | ND* | ND* |

*Not detected

TABLE 19

| Stability Data for 1.0% w/w Cream at 25° C./60% RH (15 gram aluminum tubes) | | | |
|---|---|---|---|
| | Acceptance | Time (Months) | |
| Test | Criteria | 0 mo. | 3 mo. |
| Appearance | Smooth, white emulsion | Conforms | Conforms |
| pH | Report result | 3.3 | 3.2 |
| Assay (%) | 90.0-110.0% | 102.2 | 101.7 |
| Related Substances | Report results | ND* | ND* |

*Not detected

TABLE 20

| Stability Data for 1.0% w/w Cream at 40° C./75% RH (15 gram aluminum tubes) | | | | | |
|---|---|---|---|---|---|
| | Acceptance | Time (Months) | | | |
| Test | Criteria | 0 mo. | 1 mo. | 2 mo. | 3 mo. |
| Appearance | Smooth, white emulsion | Conforms | — | — | Conforms |
| pH | Report result | 3.3 | — | — | 3.2 |
| API Assay (%) | 90.0-110.0% | 102.2 | 103.5 | 103.8 | 101.7 |
| Related Substances | Report results | ND* | ND* | ND* | ND* |

*Not detected

Example 4: Solubility Studies

In order to determine the solubility of (R)-3-(4-(7H-pyrrolo[2,3-d]pyrimidin-4-yl)-1H-pyrazol-1-yl)-3-cyclopentylpropanenitrile (free base) or its phosphate salt, approximately 5 mL of a potential solvent was added to approximately 50 mg of the API or its salt at room temperature. The mixtures were suspended and rotated on a wheel. If the mixtures became clear solutions, more solid material was added. The suspensions were then suspended over 24 hours. The samples were filtered through 0.2 micron filters. The liquid portions were collected and diluted with 50/50 water methanol/water. The concentrations of the diluted samples were analyzed by HPLC. When the free base or salt was fairly insoluble, the results are approximate only.

TABLE 21

| Potential Solvent | Solubility of Phosphate Salt (mg/mL) | Solubility of Free Base (mg/mL) |
|---|---|---|
| Water | 2.7 | 2.0 |
| pH 4, citric buffer, 0.1M | 1.5 | 1.1 |
| pH 6, citric buffer, 0.1M | 0.2 | 0.15 |
| Ethanol | 7.3 | 5.5 |
| Isopropanol | 0.6 | 0.45 |
| Benzyl alcohol | 3 | 2.3 |
| Propylene glycol | 24 | 18.2 |
| PEG 200 | 23 | 17.4 |
| PEG 300 | 14 | 10.6 |
| Glycerin | 11 | 8.3 |
| Transcutol | 10 | 7.6 |
| Trolamine | 51 | 38.6 |
| Water/PEG 200 (50/50) | 23 | 17.4 |
| Water/glyercin (50/50) | 21 | 15.9 |
| Water/glycerin/trolamine (40/40/20) | 18 | 13.6 |

TABLE 21-continued

| Potential Solvent | Solubility of Phosphate Salt (mg/mL) | Solubility of Free Base (mg/mL) |
|---|---|---|
| Isopropyl myristate | <0.1 | 0.08 |
| Isosorbide dimethyl ether | 0.4 | 0.3 |
| Mineral oil | <0.1 | 0.08 |
| Olelyl alcohol | 0.1 | 0.08 |
| Dimethicone | <0.2 | 0.15 |
| $C_{12-15}$ alcohol benzoate | <0.2 | 0.15 |
| Caprylic triglyceride | <0.2 | 0.15 |

Example 5: Other Topical Formulations

Three different topical formulations incorporating the phosphate salt of (R)-3-(4-(7H-pyrrolo[2,3-d]pyrimidin-4-yl)-1H-pyrazol-1-yl)-3-cyclopentylpropanenitrile were also prepared. The compositions of a 10% w/w dispersed cream (water-in-oil formulation), 1% w/w anhydrous ointment, and 1% w/w lotion are summarized in Table 22 (percentages are on a free base basis). Each of the formulations with 1% w/w of the phosphate salt of the API were lower in viscosity as compared to placebo (in the placebo, the balance is water). While not wishing to be bound by any particular theory, the lower viscosity was believed to be due to electrolytic nature of the phosphate salt. Viscosities of the formulations and placebo over time are shown in Table 23. The 1% dispersed cream (water-in-oil formulation) showed syneresis after two and four weeks of aging at 40° C., while the 1% lotion and 1% solubilized cream formulations (oil-in-water formulations) did not show syneresis. The 1% solubilized cream formulation was generally higher in viscosity than the 70 lotion.

TABLE 22

| Ingredient | 1% w/w lotion | 1% w/w dispersed cream | 1% w/w ointment |
|---|---|---|---|
| Purified water USP | 52.03 | 39.48 | |
| Polyethylene glycol 200 USP | 7.00 | | |
| Example 2* | 1.32 | 1.32 | 1.32 |
| Disodium EDTA USP | 0.05 | 0.50 | |
| Phenoxyethanol BP | 0.50 | 0.50 | |
| Propylene glycol USP | 15.00 | 7.50 | |
| Xanthan Gum NF | 0.20 | | |
| Methylparaben NF | 0.10 | 0.10 | |
| Propylparaben NF | 0.05 | 0.05 | |
| Light mineral oil NF | 4.00 | 6.00 | |
| Glyceryl stearate SE FDA IIG | 2.00 | | |
| Polysorbate 20 NF | 1.00 | | |
| White Petrolatum USP | 7.00 | 5.00 | 78.68 |
| Cetyl Alcohol NF | 2.50 | | |
| Stearyl Alcohol NF | 1.25 | | |
| Dimethicone NF | 1.00 | 1.00 | |
| Caprilic/capric triglycerides FDA-IIG | 5.00 | 6.00 | |
| Sodium Chloride | | 0.05 | |
| Glycerin 99% USP | | 7.50 | |
| Sorbitol solution 70% USP | | 5.00 | |
| White Wax NF | | 1.50 | |
| Hydrogenated castor oil NF | | 1.50 | |
| Cyclomethicone NF | | 12.00 | |
| Polyglyceryl-3-diisostearate NF/BP | | 5.00 | |
| Cyclomethicone (D5) NF | | | 15.00 |
| Paraffin NF | | | 5.00 |
| Total | | | |

*1.32% of (R)-3-(4-(7H-pyrrolo[2,3-d]pyrimidin-4-yl)-1H-pyrazol-1-yl)-3-cyclopentylpropanenitrile phosphate salt is 1% of the free base.

TABLE 23

| Type of | Aging | | Viscosity | | Spindle/rpm | |
|---|---|---|---|---|---|---|
| Formulation | Time | Temp. | 1% w/w API | Placebo | 1% w/w API | Placebo |
| Solubilized cream* | Initial | | 99,400 | 195,600 | T-B/2.0 | T-C/2.5 |
| | 2 weeks | RT | 67,625 | 80,125 | 27/2.0 | 27/2.0 |
| | 4 weeks | RT | 65,875 | 82,750 | 27/2.0 | 27/2.0 |
| | 2 weeks | 5° C. | 73,125 | 55,250 | 27/2.0 | 27/2.0 |
| | 4 weeks | 5° C. | 86,000 | 70,125 | 27/2.0 | 27/2.0 |
| | 2 weeks | 40° C. | 46,375 | 41,875 | 27/2.0 | 27/2.0 |
| | 4 weeks | 40° C. | 47,500 | 50,125 | 27/2.0 | 27/2.0 |
| Lotion* | Initial | | 24,700 | 70,500 | T-A/4.0 | 27/2.0 |
| | 2 weeks | RT | 28,875 | 79,250 | 27/2.0 | 27/2.0 |
| | 4 weeks | RT | 32,750 | 73,875 | 27/2.0 | 27/2.0 |
| | 2 weeks | 5° C. | 31,750 | 70,250 | 27/2.0 | 27/2.0 |
| | 4 weeks | 5° C. | 34,750 | 75,750 | 27/2.0 | 27/2.0 |
| | 2 weeks | 40° C. | 28,250 | 44,250 | 27/2.0 | 27/2.0 |
| | 4 weeks | 40° C. | 29,125 | 53,000 | 27/2.0 | 27/2.0 |
| Dispersed cream | Initial | | 11,400 | 255,500 | 27/5.0 | 28/1.0 |
| | 2 weeks | RT | 8,850 | 204,500 | 27/5.0 | 28/1.0 |
| | 4 weeks | RT | 12,200 | 208,500 | 27/5.0 | 28/1.0 |
| | 2 weeks | 5° C. | 9,550 | 226,000 | 27/5.0 | 28/1.0 |
| | 4 weeks | 5° C. | 11,200 | 238,500 | 27/5.0 | 28/1.0 |
| | 2 weeks | 40° C. | Syneresis | 185,500 | 27/5.0 | 28/1.0 |
| | 4 weeks | 40° C. | Syneresis | 185,000 | 27/5.0 | 28/1.0 |

*No syneresis observed

Example 6: Skin Permeation Studies

The three different topical formulations in Example 5 (Table 20) and the cream formulation in Example 3 (Table 4) were evaluated for transport across human cadaver skin. The skin permeation data are summarized in Table 24. Significant variability was observed in the transport among the three replicates for each formulation. The variability in transport may be due in part to differences in skin samples (donor, region of the body, thickness, etc.). In general, the two cream formulations showed higher flux compared to the lotion or ointment. The cumulative amount of API transported for the ointment formulation was particularly low in comparison to the other three formulations and this, at least in part, could be due to poor spreadability of the ointment leading to decreased surface area for transport. As a result, the two cream formulations were selected for further development, one as an oil-in-water (see Example 3 above) and the other as a water-in-oil emulsion base. Based on the solubility of the drug substance, strengths containing 1.0, 1.5, and 2.0% w/w of (R)-3-(4-(7H-pyrrolo[2,3-d]pyrimidin-4-yl)-1H-pyrazol-1-yl)-3-cyclopentylpropanenitrile phosphate salt were developed for the oil-in water base cream (solubilized cream) and 1.0, 2.0, and 3.0% w/w were developed for the water-in oil base cream (dispersed cream). Procedures for the skin permeation studies are described below.

Human Cadaver Skin Transport Studies

The permeability of the API in topical formulations was studied using cadaver human skin samples and Franz diffusion cells. Dermatomed human cadaver skin was obtained from tissue banks while the Franz diffusion cells were custom made. The human cadaver skin samples, sized to fit between the donor and the receiver compartments, were positioned on the Franz diffusion cells. Topical formulations were weighed (20 mg) onto glassine paper, placed formulation side toward the skin and clamped into place. The dosing chamber was covered with parafilm. The reservoir side was filled using saline with 4% albumin. The reservoir was stirred and maintained at 37° C. using a dry block heater (Aungst B. Fatty Acid Skin Penetration Enhancers. Pharm. Res. 1989; 6(3):244-247). At 4 hours, a 1 mL sample was removed and replaced with 1 mL of saline+4% albumin. At 24 hours, the entire reservoir was collected. The tissue was examined visually for any hole or tear. The reservoir side samples were analyzed for concentrations of the API by a LC/MS assay.

Mouse Skin Transport Studies

The permeability of the API in topical formulations was studied using freshly excised mouse skin samples mounted in Franz diffusion cells. Balb/c mice were depilated using a waxing technique four days before the experiment. The morning of the experiment the mice were euthanized and as much of the depilated skin as possible was removed, rinsed and kept moist with 37° C. saline until use. The mouse skin samples, sized to fit between the donor and the receiver compartments, were positioned between the donor and the receiver compartments of the Franz diffusion cells. The opening of the Franz cell was 1 $cm^2$. Topical formulations were weighed (20 mg) on to glassine paper, placed formulation side toward the skin and clamped into place. The dosing chamber was covered with parafilm. The reservoir side was filled using saline with 4% albumin. The reservoir was stirred and maintained at 37° C. using a dry block heater (Aungst 1989 (above). At 4 hours, a 1 mL sample was removed and replaced with 1 mL of saline+4% albumin. At 24 hours, the entire reservoir was collected. The tissue was examined visually for any hole or tear. The reservoir side samples were analyzed for concentrations of the API by a LC/MS assay.

TABLE 24

Transport of (R)-3-(4-(7H-pyrrolo[2,3-d]pyrimidin-4-yl)-1H-pyrazol-1-yl)-3-cyclopentylpropanenitrile from Topical Formulations across Human Cadaver Skin

| Strength, Type of Formulation | Human Cadaver Skin Sample | Cumulative amount over 24 h (μg) | Average cumulative amount at 24 h (μg) |
|---|---|---|---|
| 1% w/w Dispersed Cream (see Example 5, Table 20, above) | ABS #0510038 | 0.77 | 5.16 |
| | Asterand #52214A1 | 10.8 | |
| | Asterand #46581A1 | 3.91 | |

TABLE 24-continued

Transport of (R)-3-(4-(7H-pyrrolo[2,3-d]pyrimidin-4-yl)-1H-pyrazol-1-yl)-3-cyclopentylpropanenitrile from Topical Formulations across Human Cadaver Skin

| Strength, Type of Formulation | Human Cadaver Skin Sample | Cumulative amount over 24 h (μg) | Average cumulative amount at 24 h (μg) |
|---|---|---|---|
| 1% w/w Solubilized | ABS #0510038 | 0.21 | 3.73 |
| Cream | Asterand #52214A1 | 10.6 | |
| (see Example 3, | Asterand #46581A1 | 0.39 | |
| Table 4, above) | | | |
| 1% w/w Ointment | ABS #0510038 | 0.06 | 0.06 |
| (Anhydrous) | Asterand #52214A1 | 0.07 | |
| (see Example 5, | Asterand #46581A1 | 0.07 | |
| Table 20, above) | | | |
| 1% w/w Lotion | ABS #0510038 | 0.10 | 0.83 |
| (see Example 5, | Asterand #52214A1 | 1.96 | |
| Table 20, above) | Asterand #46581A1 | 0.42 | |

The effect of strength of solubilized or dispersed cream formulation on the transport of (R)-3-(4-(7H-pyrrolo[2,3-d]pyrimidin-4-yl)-1H-pyrazol-1-yl)-3-cyclopentylpropanenitrile across human cadaver skin was also examined and the data are summarized in Table 25. Increases in strength from 1% w/w to 30% w/w of the dispersed cream formulation (water-in-oil base) and 1% w/w to 2% w/w of the solubilized cream formulation (oil-in-water base) did not result in any significant change in transport of (R)-3-(4-(7H-pyrrolo[2,3-d]pyrimidin-4-yl)-1H-pyrazol-1-yl)-3-cyclopentylpropanenitrile, suggesting that the flux of (R)-3-(4-(7H-pyrrolo[2,3-d]pyrimidin-4-yl)-1H-pyrazol-1-yl)-3-cyclopentylpropanenitrile is not limited by the rate of release from each of these formulations.

TABLE 25

Transport of (R)-3-(4-(7H-pyrrolo[2,3-d]pyrimidin-4-yl)-1H-pyrazol-1-yl)-3-cyclopentylpropanenitrile from Increasing Strength Topical Formulations across Human Cadaver Skin

| Strength, Type of Formulation | Human Cadaver Skin Sample | Cumulative Amount over 24 h (μg) | Average Cumulative Amount at 24 h (μg) |
|---|---|---|---|
| 1% w/w Dispersed | ABS #0510038 | 1.26 | 2.29 |
| Cream | Asterand #42996A1 | 3.31 | |
| (water-in-oil base) | | | |
| 2% w/w Dispersed | ABS #0510038 | 1.79 | 1.68 |
| Cream | Asterand #42996A1 | 1.56 | |
| (water-in-oil base) | | | |
| 3% w/w Dispersed | ABS #0510038 | 1.40 | 1.81 |
| Cream | Asterand #42996A1 | 2.23 | |
| (water-in-oil base) | | | |
| 1% w/w | ABS #0510038 | 0.17 | 0.89 |
| Solubilized Cream | Asterand #42996A1 | 1.62 | |
| (see Example 3 above) | | | |
| 1.5% w/w | ABS #0510038 | 0.21 | 0.30 |
| Solubilized Cream | Asterand #42996A1 | 0.39 | |
| (see Example 3 above) | | | |
| 2% w/w | ABS #0510038 | 0.24 | 0.25 |
| Solubilized Cream | Asterand #42996A1 | 0.26 | |

The transport of (R)-3-(4-(7H-pyrrolo[2,3-d]pyrimidin-4-yl)-1H-pyrazol-1-yl)-3-cyclopentylpropanenitrile across freshly excised mouse skin was also evaluated using formulations that were employed in rodent pharmacology studies (Table 26). There was a general trend of increased permeability when the strength of the solubilized cream was increased from 0.5 to 1.5%, while such a trend was not seen with the dispersed formulation. For the solubilized cream, the average cumulative amount of (R)-3-(4-(7H-pyrrolo[2,3-d]pyrimidin-4-yl)-1H-pyrazol-1-yl)-3-cyclopentylpropanenitrile transported across mouse skin over 24 h was about twenty times higher than that seen with human cadaver skin studies (cumulative average of all experiments).

Based on the solubility of (R)-3-(4-(7H-pyrrolo[2,3-d]pyrimidin-4-yl)-1H-pyrazol-1-yl)-3-cyclopentylpropanenitrile phosphate, a maximum drug loading of 1.5% was possible with the oil-in-water (solubilized cream) formulation. Of the two creams formulated, the oil in water (solubilized cream) product exhibited better physical stability (see Table 21 above). It should be noted that strengths higher than 3% in the dispersed cream formulation and 2% in the solubilized cream formulation were not physically stable beyond several days of storage at controlled room temperature, as the drug substance crystallized out of solution. Based on these findings, coupled with skin permeability results, manufacturability data, and physical and chemical characterization data obtained for the early stage formulations, a solubilized cream with an oil-in water emulsion base (with a maximum strength of 1.5% w/w) was chosen for further development.

TABLE 26

Transport of Various Formulations of (R)-3-(4-(7H-pyrrolo[2,3-d]pyrimidin-4-yl)-1H-pyrazol-1-yl)-3-cyclopentylpropanenitrile across Freshly Excised Mouse Skin

| Strength, Formulation | Cumulative Amount over 24 h (μg) | Average Cumulative amount at 24 h (μg) |
|---|---|---|
| 1% w/w dispersed cream | 37.1 | 42.0 |
| (water-in-oil base) | 46.9 | |
| 1% w/w dispersed cream | 18.0 | 23.1 |
| (water-in-oil base) | 28.2 | |
| 3% w/w dispersed cream | 29.6 | 29.8 |
| (water-in-oil base) | 30.0 | |
| 0.5% w/w solubulized cream | 26.5 | 23.5 |
| (see Example 3 above) | 20.4 | |
| 1% w/w solubulized cream | 40.8 | 32.8 |
| (see Example 3 above) | 24.9 | |
| 1.5% w/w solubulized cream | 44.6 | 41.8 |
| (see Example 3 above) | 38.9 | |

Example 7: Clinical Treatment of Psoriasis with Formulations

Figure 2:
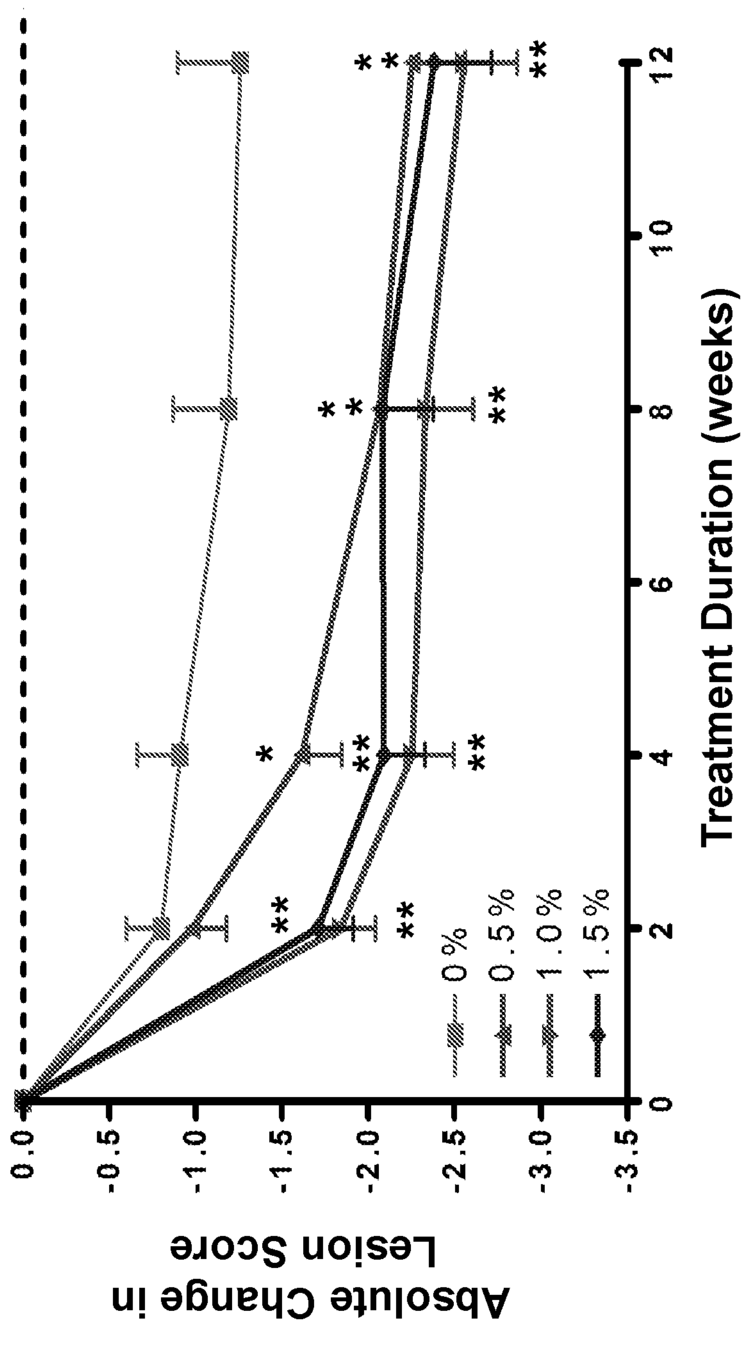
FIG. 2 depicts the change in lesion score for subjects with chronic plaque psoriasis treated with 0.5%, 1.0%, and 1.5% w/w of an oil-in-water formulation of (R)-3-(4-(7H-pyrrolo[2,3-d]pyrimidin-4-yl)-1H-pyrazol-1-yl)-3-cyclopentylpropanenitrile phosphoric acid salt (on a free base basis) as compared to treatment with placebo over a 12-week period (the dashed line is baseline).
Figure 3:
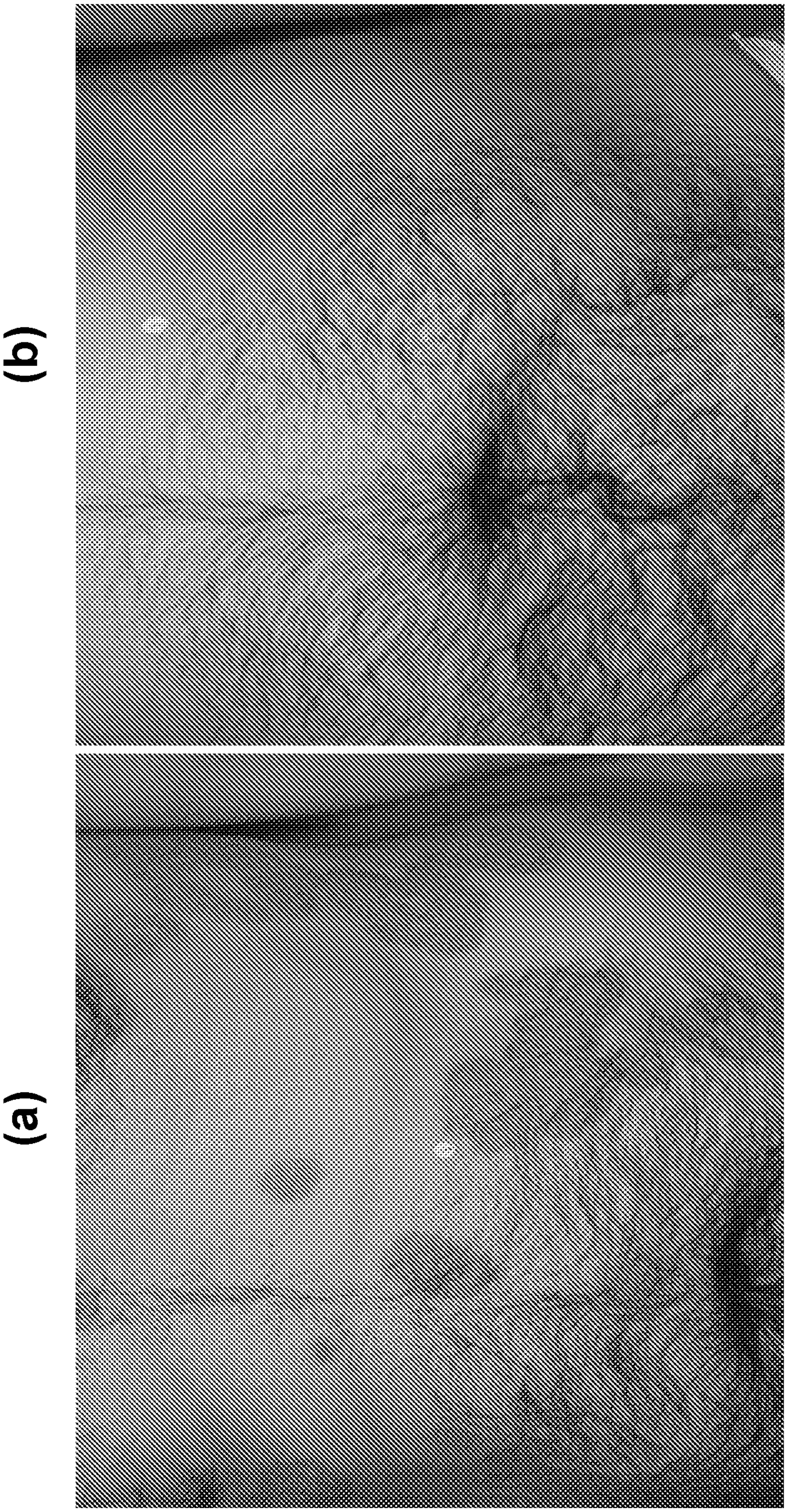
FIG. 3 shows photographs of subjects with chronic plaque psoriasis before (FIG. 3(*a*)) and after 84 days (FIG. 3(*b*)) of treatment with 1.0% w/w of an oil-in-water formulation of (R)-3-(4-(7H-pyrrolo[2,3-d]pyrimidin-4-yl)-1H-pyrazol-1-yl)-3-cyclopentylpropanenitrile phosphoric acid salt (on a free base basis).
Figure 4:
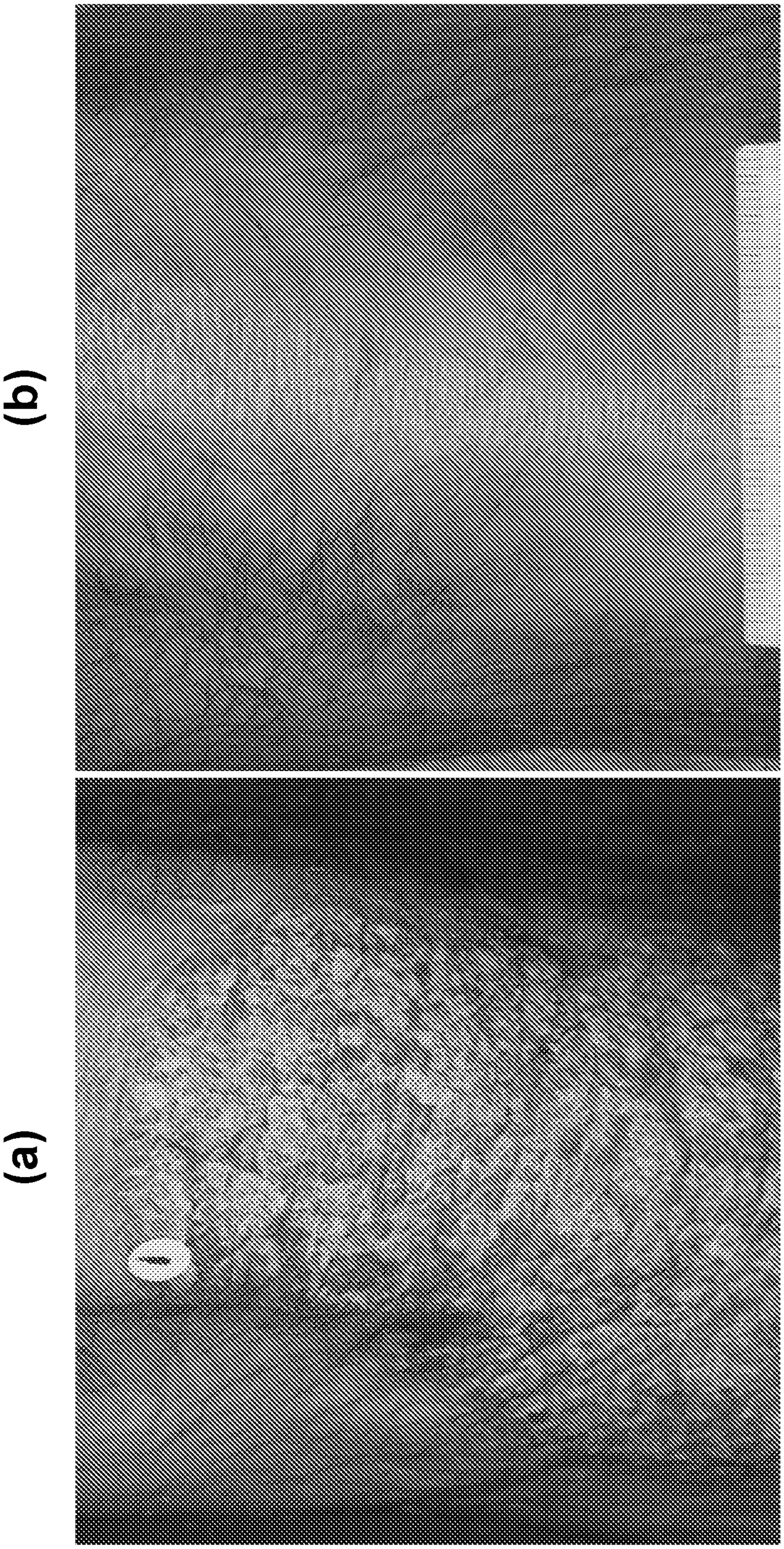
FIG. 4 shows photographs of subjects with chronic plaque psoriasis before (FIG. 4(*a*)) and after 84 days (FIG. 4(*b*)) of treatment with 1.0% w/w of an oil-in-water formulation of (R)-3-(4-(7H-pyrrolo[2,3-d]pyrimidin-4-yl)-1H-pyrazol-1-yl)-3-cyclopentylpropanenitrile phosphoric acid salt (on a free base basis).
Figure 5:
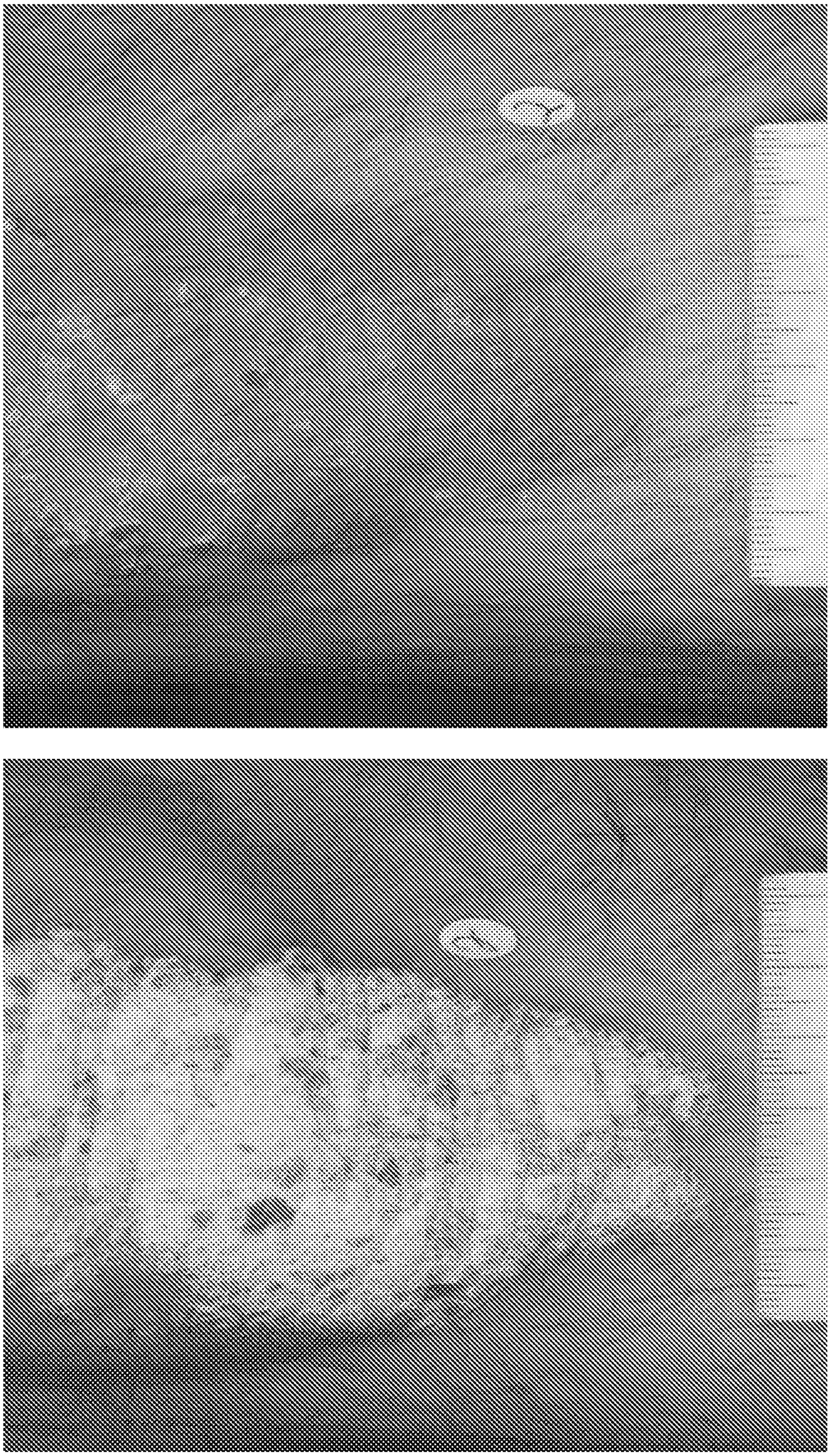
FIG. 5 shows photographs of subjects with chronic plaque psoriasis before (FIG. 5(*a*)) and after 84 days (FIG. 5(*b*)) of treatment with 1.5% w/w of an oil-in-water formulation of (R)-3-(4-(7H-pyrrolo[2,3-d]pyrimidin-4-yl)-1H-pyrazol-1-yl)-3-cyclopentylpropanenitrile phosphoric acid salt (on a free base basis).
Figure 6:
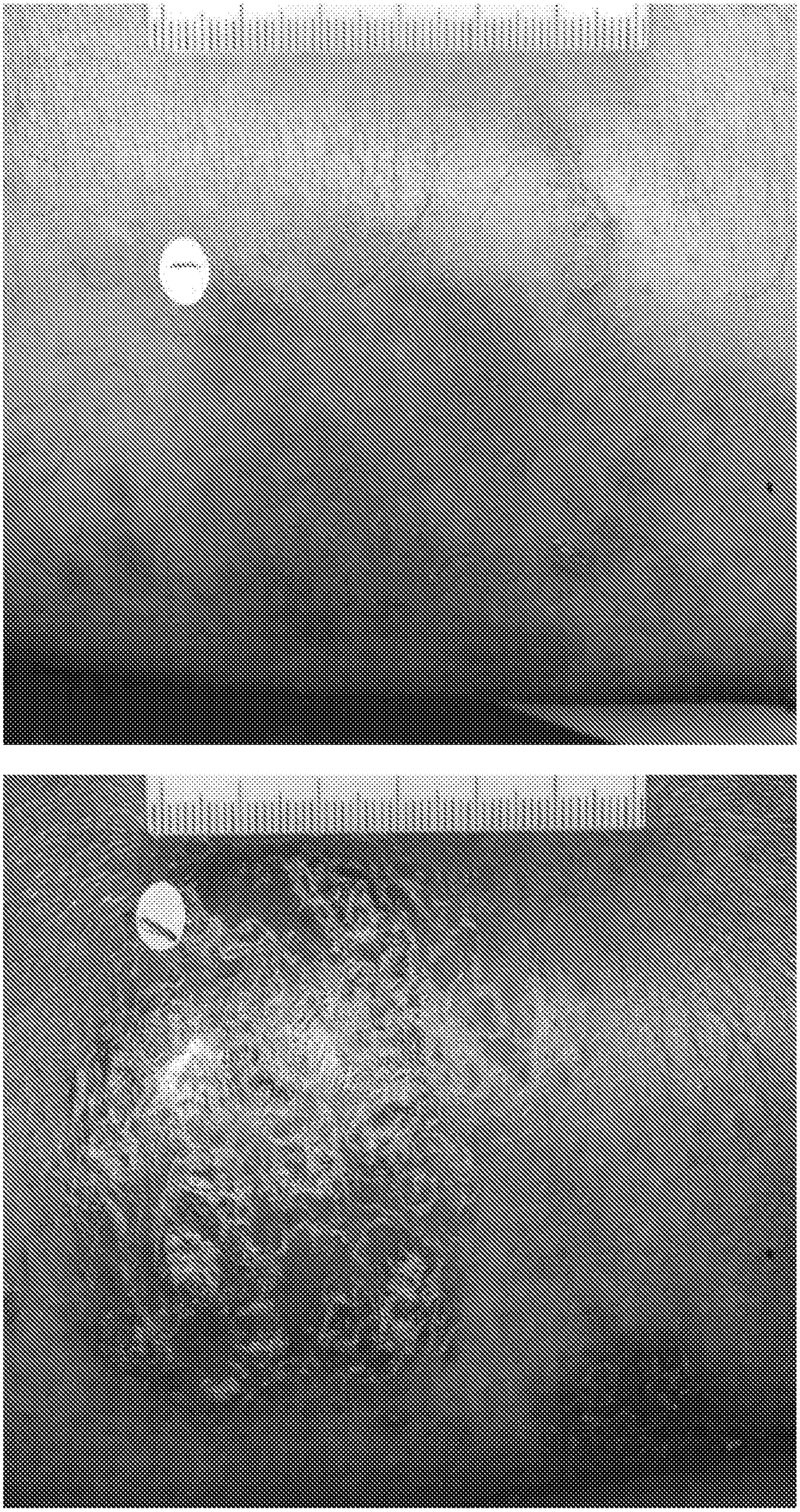
FIG. 6 shows photographs of subjects with chronic plaque psoriasis before (FIG. 6(*a*)) and after 84 days (FIG. 6(*b*)) of treatment with 0.5% w/w of an oil-in-water formulation of (R)-3-(4-(7H-pyrrolo[2,3-d]pyrimidin-4-yl)-1H-pyrazol-1-yl)-3-cyclopentylpropanenitrile phosphoric acid salt (on a free base basis).
Figure 7:
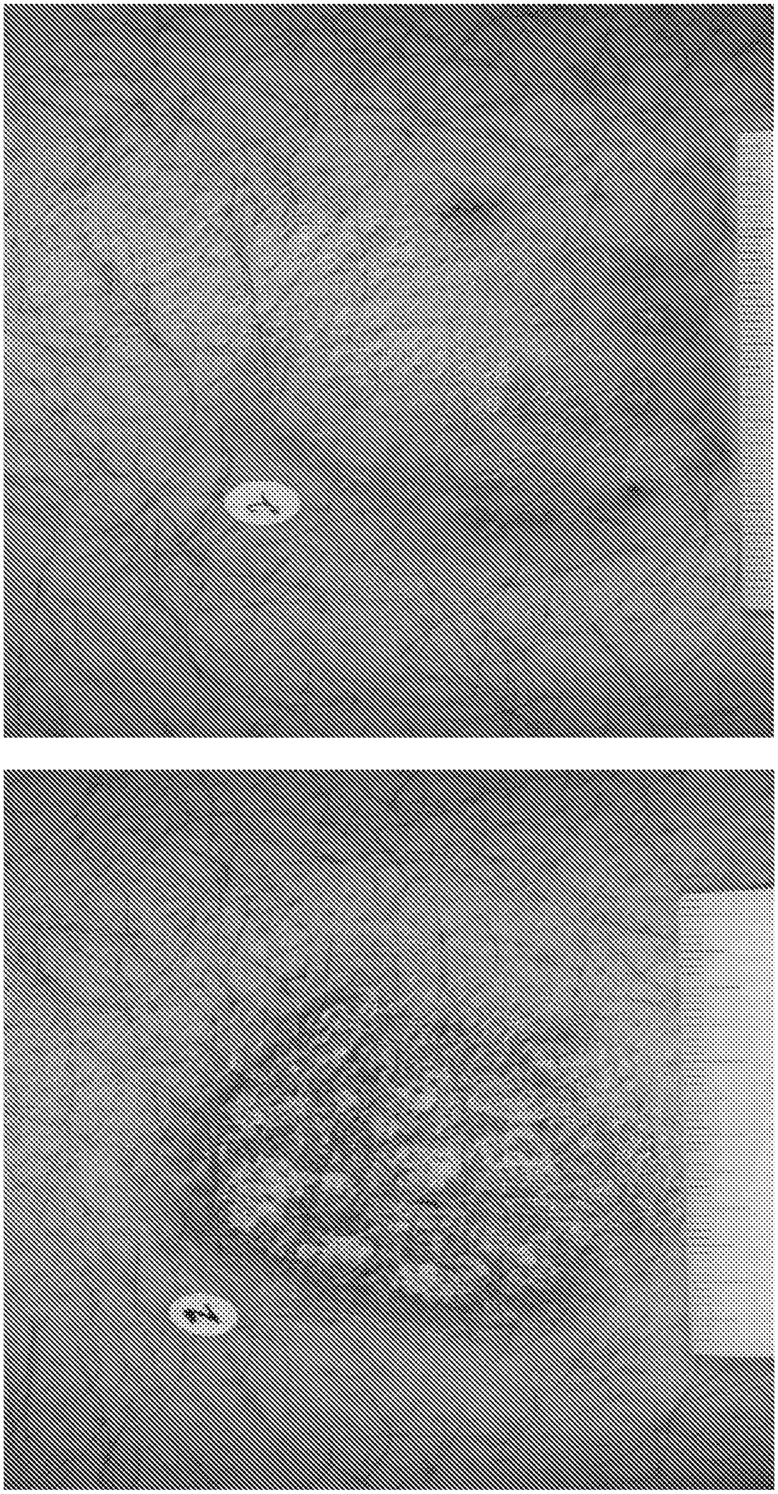
FIG. 7 shows photographs of subjects with chronic plaque psoriasis before (FIG. 7(*a*)) and after 84 days (FIG. 7(*b*)) of treatment with 1.0% w/w of an oil-in-water formulation of (R)-3-(4-(7H-pyrrolo[2,3-d]pyrimidin-4-yl)-1H-pyrazol-1-yl)-3-cyclopentylpropanenitrile phosphoric acid salt (on a free base basis).

Approximately 200 subjects with chronic plaque psoriasis were enrolled in a double-blind, placebo-controlled study. There were four dose groups, three active treatment groups and vehicle. The active treatment groups were treated with the 0.5%, 1.0%, and 1.5% w/w oil-in-water formulations (see Example 3 supra). Approximately 50 subjects were randomized into each treatment group. A thin layer of cream was applied once per day to up to 20% body surface area of plaque psoriasis. Treatment was applied for 84 days and efficacy measured by the change in total lesion score, a measurement scale which assesses the amount of erythema, scaling and thickness of the plaques (FIG. 2). 25% of patents randomized to 1% w/w or 1.5% w/w of the API had lesions that were clear or almost clear at week 12, versus 6% on vehicle.

At a subset of sites, photos were obtained from subjects who signed an informed consent for the photos. Pictures were obtained at baseline (prior to the first application of study treatment) and on day 84 (the last application day for study treatment) (see FIG. 3-7). These photos are representative of a subset of the subjects who were treated with the oil-in-water formulations.

Example 8: Murine Skin Contact Delayed Hypersensitivity Response Test

The formulations described herein can also be tested for their efficacies (of inhibiting JAK targets) in the T-cell driven murine delayed hypersensitivity test model. The murine skin contact delayed-type hypersensitivity (DTH) response is considered to be a valid model of clinical contact dermatitis, and other T-lymphocyte mediated immune disorders of the skin, such as psoriasis (Immunol Today. 1998 January; 19(1):37-44). Murine DTH shares multiple characteristics with psoriasis, including the immune infiltrate, the accompanying increase in inflammatory cytokines, and keratinocyte hyperproliferation. Furthermore, many classes of agents that are efficacious in treating psoriasis in the clinic are also effective inhibitors of the DTH response in mice (Agents Actions. 1993 January; 38(1-2):116-21).

On Day 0 and 1, Balb/c mice are sensitized with a topical application, to their shaved abdomen with the antigen 2,4, dinitro-fluorobenzene (DNFB). On day 5, ears are measured for thickness using an engineer's micrometer. This measurement is recorded and used as a baseline. Both of the animals' ears are then challenged by a topical application of DNFB in a total of 20 μL (10 μL on the internal pinna and 10 μL on the external pinna) at a concentration of 0.2%. Twenty-four to seventy-two hours after the challenge, ears are measured again. Treatment with the test formulations is given throughout the sensitization and challenge phases (day −1 to day 7) or prior to and throughout the challenge phase (usually afternoon of day 4 to day 7). Treatment of the test compounds (in different concentration) is administered topically (topical application of the treatment to the ears). Efficacies of the test formulations are indicated by a reduction in ear swelling comparing to the situation without the treatment. Compounds causing a reduction of 20% or more are considered efficacious. In some experiments, the mice are challenged but not sensitized (negative control).

The inhibitive effect (inhibiting activation of the JAK-STAT pathways) of the test formulations can be confirmed by immunohistochemical analysis. Activation of the JAK-STAT pathway(s) results in the formation and translocation of functional transcription factors. Further, the influx of immune cells and the increased proliferation of keratinocytes should also provide unique expression profile changes in the ear that can be investigated and quantified. Formalin fixed and paraffin embedded ear sections (harvested after the challenge phase in the DTH model) are subjected to immunohistochemical analysis using an antibody that specifically interacts with phosphorylated STAT3 (clone 58E12, Cell Signaling Technologies). The mouse ears are treated with test formulations, vehicle, or dexamethasone (a clinically efficacious treatment for psoriasis), or without any treatment, in the DTH model for comparisons. Test formulations and the dexamethasone can produce similar transcriptional changes both qualitatively and quantitatively, and both the test formulations and dexamethasone can reduce the number of infiltrating cells. Topical administration of the test compounds can produce inhibitive effects, i.e., reduction in the number of infiltrating cells and inhibition of the transcriptional changes.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

What is claimed is:

1. A pharmaceutical composition for topical skin application to a human patient, comprising:
(1) about 0.5% to about 1.5% by weight of the composition, on a free base basis, of 1:1 (R)-3-cyclopentyl-3-[4 (7H-pyrrolo[2,3-d]pyrimidin-4-yl)-1H-pyrazol-1-yl]propanenitrile phosphoric acid salt, and
(2) a means for effecting skin permeation of the (R)-3-cyclopentyl-3-[4 (7H-pyrrolo[2,3-d]pyrimidin-4-yl)-1H-pyrazol-1-yl]propanenitrile to the patient.

2. The composition according to claim 1, wherein the composition is for application to the patient's skin for up to 84 consecutive days.

3. A pharmaceutical composition for topical skin application to a human patient, comprising:
(1) about 0.5% by weight of the composition, on a free base basis, of 1:1 (R)-3-cyclopentyl-3-[4 (7H-pyrrolo[2,3-d]pyrimidin-4-yl)-1H-pyrazol-1-yl]propanenitrile phosphoric acid salt, and
(2) a means for effecting skin permeation of the (R)-3-cyclopentyl-3-[4 (7H-pyrrolo[2,3-d]pyrimidin-4-yl)-1H-pyrazol-1-yl]propanenitrile to the patient.

4. A pharmaceutical composition for topical skin application to a human patient, comprising:
(1) about 1.0% by weight of the composition, on a free base basis, of 1:1 (R)-3-cyclopentyl-3-[4 (7H-pyrrolo[2,3-d]pyrimidin-4-yl)-1H-pyrazol-1-yl]propanenitrile phosphoric acid salt, and
(2) a means for effecting skin permeation of the (R)-3-cyclopentyl-3-[4 (7H-pyrrolo[2,3-d]pyrimidin-4-yl)-1H-pyrazol-1-yl]propanenitrile to the patient.

5. A pharmaceutical composition for topical skin application to a human patient, comprising:
(1) about 1.5% by weight of the composition, on a free base basis, of 1:1 (R)-3-cyclopentyl-3-[4 (7H-pyrrolo[2,3-d]pyrimidin-4-yl)-1H-pyrazol-1-yl]propanenitrile phosphoric acid salt, and
(2) a means for effecting skin permeation of the (R)-3-cyclopentyl-3-[4 (7H-pyrrolo[2,3-d]pyrimidin-4-yl)-1H-pyrazol-1-yl]propanenitrile to the patient.

6. The composition according to claim 1, wherein the patient has a skin disorder.

7. The composition according to claim 6, wherein the skin disorder is an autoimmune skin disorder.

8. The composition according to claim 6, wherein the skin disorder is associated with JAK1 and/or JAK2.

9. The composition according to claim 6, wherein the skin disorder is chosen from pemphigus vulgaris (PV), bullous pemphigoid (BP), psoriasis, psoriasis vulgaris, atopic dermatitis, and combinations thereof.

10. The composition according to claim 6, wherein the skin disorder is atopic dermatitis.

* * * * *